US010118959B2

(12) United States Patent
Lazar et al.

(10) Patent No.: US 10,118,959 B2
(45) Date of Patent: *Nov. 6, 2018

(54) ANTI-GLYPICAN-3 ANTIBODY

(71) Applicants: Xencor, Inc., Monrovia, CA (US); Chugai Seiyaku Kabushiki Kaisha, Tokyo (JP)

(72) Inventors: Gregory Alan Lazar, Los Angeles, CA (US); Bassil I. Dahiyat, Altadena, CA (US); Hisafumi Okabe, Kanagawa (JP); Masamichi Sugimoto, Kanagawa (JP); Shigeyuki Iijima, Shizuoka (JP); Izumi Sugo, Shizuoka (JP)

(73) Assignees: Chugai Seiyaku Kabushiki Kaisha, Tokyo (JP); Xencor, Inc., Monrovia, CA (US)

( * ) Notice: Subject to any disclaimer, the term of this patent is extended or adjusted under 35 U.S.C. 154(b) by 625 days.

This patent is subject to a terminal disclaimer.

(21) Appl. No.: 14/505,932

(22) Filed: Oct. 3, 2014

(65) Prior Publication Data

US 2015/0098941 A1  Apr. 9, 2015

Related U.S. Application Data

(63) Continuation of application No. 11/251,561, filed on Oct. 14, 2005, now abandoned.

(51) Int. Cl.

| *C07K 16/00* | (2006.01) |
|---|---|
| *C12P 21/08* | (2006.01) |
| *A61K 39/395* | (2006.01) |
| *A61K 39/40* | (2006.01) |
| *C07K 16/18* | (2006.01) |
| *C07K 16/30* | (2006.01) |
| *C07K 1/00* | (2006.01) |
| *A61K 39/00* | (2006.01) |

(52) U.S. Cl.
CPC ............ *C07K 16/18* (2013.01); *C07K 16/303* (2013.01); *A61K 2039/505* (2013.01); *C07K 2317/24* (2013.01); *C07K 2317/52* (2013.01); *C07K 2317/524* (2013.01); *C07K 2317/526* (2013.01); *C07K 2317/732* (2013.01)

(58) Field of Classification Search
None
See application file for complete search history.

(56) References Cited

U.S. PATENT DOCUMENTS

| 5,322,678 | A | 6/1994 | Morgan et al. |
|---|---|---|---|
| 5,530,101 | A | 6/1996 | Queen et al. |
| 6,165,745 | A | 12/2000 | Ward et al. |
| 6,210,670 | B1 | 4/2001 | Berg |
| 6,436,411 | B1 | 8/2002 | Riordan et al. |
| 6,617,156 | B1 | 9/2003 | Doucette-Stamm et al. |
| 6,737,056 | B1 * | 5/2004 | Presta ............... C07K 16/28 424/133.1 |
| 7,297,775 | B2 * | 11/2007 | Idusogie ........ A61K 47/48561 530/387.1 |
| 7,317,091 | B2 * | 1/2008 | Lazar ............... C07K 16/22 530/387.1 |
| 7,361,336 | B1 | 4/2008 | Bergstein |
| 7,427,400 | B2 | 9/2008 | Bergstein |
| 7,662,925 | B2 | 2/2010 | Lazar et al. |
| 7,691,586 | B2 | 4/2010 | Watanabe et al. |
| 7,744,880 | B2 | 6/2010 | Aburatani et al. |
| 7,867,734 | B2 | 1/2011 | Nakano et al. |
| 7,871,613 | B2 | 1/2011 | Kinoshita et al. |
| 7,919,086 | B2 | 4/2011 | Nakano et al. |
| 8,039,592 | B2 | 10/2011 | Lazar et al. |
| 8,263,077 | B2 | 9/2012 | Aburatani et al. |
| 8,497,355 | B2 | 7/2013 | Igawa et al. |
| 8,663,929 | B2 | 3/2014 | Kataoka et al. |
| 8,937,158 | B2 * | 1/2015 | Lazar ............... C07K 16/00 530/387.1 |
| 9,096,651 | B2 | 8/2015 | Igawa et al. |
| 9,102,739 | B2 * | 8/2015 | Lazar ............. C07K 16/303 |
| 9,513,292 | B2 | 12/2016 | Aburatani et al. |
| 2002/0102254 | A1 | 8/2002 | Leung et al. |

(Continued)

FOREIGN PATENT DOCUMENTS

| CA | 2451493 | 1/2003 |
|---|---|---|
| CA | 2481658 | 10/2003 |

(Continued)

OTHER PUBLICATIONS

Lazar declaration, Dec. 27, 2010, pp. 1-4.*
Kabat et al., Sequences of Proteins of Immunological Interest, vol. 1, 5th Edition (1991).
USPTO Office Action in U.S. Appl. No. 12/797,349, dated Jul. 27, 2015, 7 pages.
Khaldoun Almhanna et al., "Treatment Approaches for Hepatocellular Carcinoma," Clinical Medicine: Oncology, 11-19 (2007).
Roitt et al., "Immunology," 150-152 (2000).

(Continued)

*Primary Examiner* — Chun W Dahle
(74) *Attorney, Agent, or Firm* — Fish & Richardson P.C.

(57) ABSTRACT

An anti-glypican-3 antibody comprising one or more amino acid substitutions introduced in the Fc region is disclosed. Preferably, in the anti-glypican-3 antibody, one or more of the amino acid residues at the positions 239, 298, 326, 330 and 332 in the Fc region are substituted with other amino acid residues. Since the Fc-modified anti-glypican-3 antibody of the invention exhibit enhanced ADCC activity, it is useful in treating cancers, such as hepatic cancer. Also disclosed are an anticancer agent comprising the anti-glypican-3 antibody of the invention and a pharmaceutically acceptable carrier, as well as a method of treating a patient with cancer comprising administering to the patient the anticancer agent of the invention.

10 Claims, 5 Drawing Sheets

Specification includes a Sequence Listing.

(56) References Cited

U.S. PATENT DOCUMENTS

| | | |
|---|---|---|
| 2003/0103970 A1 | 6/2003 | Tsuchiya et al. |
| 2003/0175884 A1 | 9/2003 | Umana et al. |
| 2003/0195211 A1 | 10/2003 | Sadhu et al. |
| 2004/0022793 A1 | 2/2004 | Severn et al. |
| 2004/0024320 A1 | 2/2004 | Karasawa et al. |
| 2004/0110226 A1* | 6/2004 | Lazar .......... C07K 16/00 435/7.1 |
| 2004/0132101 A1 | 7/2004 | Lazar et al. |
| 2004/0236080 A1 | 11/2004 | Aburatani et al. |
| 2005/0054832 A1* | 3/2005 | Lazar .......... C07K 16/22 530/387.3 |
| 2005/0171339 A1 | 8/2005 | Sugo et al. |
| 2005/0233392 A1 | 10/2005 | Filmus et al. |
| 2006/0014223 A1 | 1/2006 | Aburatani et al. |
| 2006/0024298 A1 | 2/2006 | Lazar et al. |
| 2006/0040325 A1* | 2/2006 | Wu .......... C07K 16/00 435/7.1 |
| 2006/0167232 A1 | 7/2006 | Aburatani et al. |
| 2006/0188510 A1 | 8/2006 | Aburatani et al. |
| 2006/0246550 A1 | 11/2006 | Okumura |
| 2006/0287508 A1 | 12/2006 | Sugo et al. |
| 2007/0087005 A1 | 4/2007 | Lazar et al. |
| 2007/0172488 A1 | 7/2007 | Aburatani et al. |
| 2007/0190599 A1 | 8/2007 | Nakano et al. |
| 2007/0269444 A1 | 11/2007 | Kinoshita et al. |
| 2008/0008710 A1 | 1/2008 | Aburatani et al. |
| 2008/0051563 A1 | 2/2008 | Lazar et al. |
| 2008/0124330 A1 | 5/2008 | Nakano et al. |
| 2008/0138827 A1 | 6/2008 | Watanabe et al. |
| 2008/0154025 A1 | 6/2008 | Lazar et al. |
| 2008/0161541 A1 | 7/2008 | Lazar et al. |
| 2008/0166756 A1 | 7/2008 | Tsuchiya et al. |
| 2008/0181890 A1 | 7/2008 | Lazar et al. |
| 2008/0267979 A1 | 10/2008 | Lazar et al. |
| 2009/0028868 A1 | 1/2009 | Fujiwara et al. |
| 2009/0060907 A1 | 3/2009 | Aburatani et al. |
| 2010/0167315 A1 | 7/2010 | Thibault et al. |
| 2010/0183595 A1 | 7/2010 | Aburatani et al. |
| 2010/0239577 A1 | 9/2010 | Igawa et al. |
| 2010/0248359 A1 | 9/2010 | Nakano et al. |
| 2011/0033452 A1 | 2/2011 | Nakano et al. |
| 2011/0076275 A1 | 3/2011 | Igawa et al. |
| 2011/0091907 A1 | 4/2011 | Kataoka et al. |
| 2011/0104157 A1 | 5/2011 | Kinoshita et al. |
| 2015/0210763 A1 | 7/2015 | Kuramochi et al. |
| 2015/0259417 A1 | 9/2015 | Nakano et al. |
| 2015/0285806 A1 | 10/2015 | Ohtomo et al. |
| 2015/0315278 A1 | 11/2015 | Igawa et al. |

FOREIGN PATENT DOCUMENTS

| | | |
|---|---|---|
| CA | 2497744 | 3/2004 |
| CA | 2801911 | 3/2004 |
| CN | 1277632 | 12/2000 |
| CN | 1440295 | 9/2003 |
| CN | 1440408 | 9/2003 |
| CN | 1678740 | 10/2005 |
| CN | 101377506 | 3/2009 |
| CN | 102046200 | 5/2011 |
| CN | 102276721 | 12/2011 |
| EP | 0 329 185 | 8/1989 |
| EP | 1 176 195 | 1/2002 |
| EP | 1 331 266 | 7/2003 |
| EP | 1 411 118 | 4/2004 |
| EP | 1 462 799 | 9/2004 |
| EP | 1 464 702 | 10/2004 |
| EP | 1 498 491 | 1/2005 |
| EP | 1 541 680 | 6/2005 |
| EP | 1 541 686 | 6/2005 |
| EP | 1 548 442 | 6/2005 |
| EP | 1 561 686 | 8/2005 |
| EP | 1 671 645 | 6/2006 |
| EP | 1 674 111 | 6/2006 |
| EP | 1 780 273 | 5/2007 |
| EP | 1 800 693 | 6/2007 |
| EP | 1 816 140 | 8/2007 |
| EP | 1 829 962 | 9/2007 |
| EP | 2 937 697 | 10/2015 |
| JP | H02028200 | 1/1990 |
| JP | 2-42355 | 2/1990 |
| JP | 4-336051 | 11/1992 |
| JP | 11-118775 | 4/1999 |
| JP | 2001-108661 | 4/2001 |
| JP | 2002-48867 | 2/2002 |
| JP | 2003-149213 | 5/2003 |
| JP | 2004-053360 | 2/2004 |
| JP | 2004-503582 | 2/2004 |
| JP | 2007-093274 | 4/2007 |
| JP | 2008-501677 | 1/2008 |
| JP | 2011068682 | 4/2011 |
| JP | 2015-511702 | 4/2015 |
| KR | 10-2007-0034448 | 3/2007 |
| RU | 2001124907 | 2/2000 |
| WO | WO 93/22332 | 11/1993 |
| WO | WO 98/23289 | 6/1998 |
| WO | WO 99/54342 | 10/1999 |
| WO | WO 00/47228 | 8/2000 |
| WO | WO 00/61739 | 10/2000 |
| WO | WO 02/05791 | 1/2001 |
| WO | WO 02/22739 | 3/2002 |
| WO | WO 02/31140 | 4/2002 |
| WO | WO 02/40545 | 5/2002 |
| WO | WO 02/079255 | 10/2002 |
| WO | WO 03/000883 | 1/2003 |
| WO | WO 03/042686 | 5/2003 |
| WO | WO 03/057881 | 7/2003 |
| WO | WO 03/074679 | 9/2003 |
| WO | WO 03/085119 | 10/2003 |
| WO | WO 03/100429 | 12/2003 |
| WO | WO 2004/018667 | 3/2004 |
| WO | WO 2004/022597 | 3/2004 |
| WO | WO 2004/022739 | 3/2004 |
| WO | WO 2004/022754 | 3/2004 |
| WO | WO 2004/023145 | 3/2004 |
| WO | WO 2004/029207 | 4/2004 |
| WO | WO 2004/038420 | 5/2004 |
| WO | WO 2004/099249 | 11/2004 |
| WO | WO 2005/023301 | 3/2005 |
| WO | WO 2005/106485 | 10/2005 |
| WO | WO 05/117980 | 12/2005 |
| WO | WO 2006/006693 | 1/2006 |
| WO | WO 2006/022407 | 3/2006 |
| WO | WO 2006/046751 | 5/2006 |
| WO | WO 2006/066171 | 6/2006 |
| WO | WO 2006/067913 | 6/2006 |
| WO | WO 2007/005612 | 1/2007 |
| WO | WO 2007/047291 | 4/2007 |
| WO | WO 07/053573 | 5/2007 |
| WO | WO 07/059782 | 5/2007 |
| WO | WO 07/091622 | 8/2007 |
| WO | WO 07/099988 | 9/2007 |
| WO | WO 2007/137170 | 11/2007 |
| WO | WO 2008/032217 | 3/2008 |
| WO | WO 2009/041062 | 4/2009 |
| WO | WO 2009/041643 | 4/2009 |
| WO | WO 2009/116659 | 9/2009 |
| WO | WO 2009/122667 | 10/2009 |
| WO | WO 2009/149185 | 12/2009 |
| WO | WO 2012/145469 | 10/2012 |
| WO | WO 2013/118858 | 8/2013 |
| WO | WO 2013/127465 | 9/2013 |

OTHER PUBLICATIONS

Office Action for Israeli App. Ser. No. 208451, dated Nov. 24, 2015 (with English translation), 7 pages.

Office Action for Chinese App. Ser. No. 201380067139.1, dated Jan. 4, 2016, 11 pages.

Notice of Allowance for Korean App. Ser. No. 20107008895, dated Jan. 4, 2016 (with English translation), 4 pages.

Office Action for Russian App. Ser. No. 2011115845, dated Oct. 7, 2015 (with English translation), 9 pages.

(56) References Cited

OTHER PUBLICATIONS

USPTO Non-Final Office Action in U.S. Appl. No. 12/852,950, dated Nov. 13, 2015, 33 pages.
Hopfner et al., "Growth factor receptors and related signalling pathways as targets for novel treatment strategies of hepatocellular cancer," World J Gastroenterol., Jan. 7, 2008;14(1):1-14.
Krusch et al., "The kinase inhibitors Sunitinib and Sorafenib differentially affect reactivity of NK cells against Renal Cell Cancer," The FASEB Journal, 2008;22:1077.5.
Nexavar (sorafenib) tablets, prescribing information, © 2007 Bayer Pharmaceuticals Corporation, 17 pages.
Zhu, "Development of Sorafenib and Other Molecularly Targeted Agents in Hepatocellular Carcinoma," Cancer, Jan. 15, 2008; 112(2):250-9.
USPTO Office Action in U.S. Appl. No. 12/936,367, dated Feb. 18, 2016, 27 pages.
Notice of Allowance for Korean App. Ser. No. 10-2010-7024691, dated Feb. 22, 2016 (with English translation), 3 pages.
Ikeda et al., "Drug therapy for Primary Liver Cancer and Kinase Inhibitor Sorafenib," Hematology & Oncology, 56:70-75 (2008) with English translation.
Konno et al., "Fucose content of monoclonal antibodies can be controlled by culture medium osmolality for high antibody-dependent cellular cytotoxicity," Cytotechnology, 64:249-265 (2012).
Kunkel et al., "Comparisons of the Glycosylation of a Monoclonal Antibody Produced under Nominally Identical Cell Culture Conditions in Two Different Bioreactors," Biotechnol. Prog., 16:462-470 (2000).
Lake et al., "Immunotherapy and chemotherapy—a practical partnership," Nature Reviews, 5:397-405 (2005).
Raju, "Glycosylation Variations with Expression Systems and Their Impact on Biological Activity of Therapeutic Immunoglobulins," BioProcess International, pp. 44-53 (2003).
Office Action for Costa Rica App. Ser. No. 11769, dated Mar. 11, 2016 (no English translation), 10 pages.
Office Action for European App. Ser. No. 12179554.6, dated Mar. 4, 2016, 5 pages.
Office Action for Singapore App. Ser. No. 2013025549, dated Mar. 7, 2016, 6 pages.
Summons to attend oral proceedings pursuant to Rule 115(1) EPC for European App. Ser. No. 05800031.6, dated Mar. 4, 2016, 8 pages.
Office Action for European App. Ser. No. 15153329.6, dated Jun. 22, 2016, 6 pages.
USPTO Office Action in U.S. Appl. No. 10/526,741, dated Jun. 8, 2016, 44 pages.
Endo, "A novel molecular targeted therapy, humanized anti-glypican 3 antibody (GC33), for the treatment of unresectable hepatocellular cancer," Medical Science Digest, Aug. 25, 2013;39(9):440-443 (with English translation).
Hashiguchi et al., "Using immunofluorescent digital slide technology to quantify protein expression in archival paraffin-embedded tissue sections," Pathol Int., Nov. 2010;60(11):720-5. doi: 10.1111/j.1440-1827.2010.02590.x. Epub Aug. 17, 2010.
Ikeda et al., "Japanese phase I study of GC33, a humanized antibody against glypican-3 for advanced hepatocellular carcinoma," Cancer Sci, Apr. 2014;105(4):455-62. doi: 10.1111/cas.12368. Epub Mar. 25, 2014.
International Search Report for App. Ser. No. PCT/JP2016/069493, dated Sep. 20, 2016, 4 pages.
Kawaida et al., "Proceedings of the Japanese Society of Pathology," 104th Conference of the Japanese Society of Pathology—Nagoya Congress Center, Mar. 23, 2015;104(1):324 (with English translation).
Zhu et al., "First-in-man phase I study of GC33, a novel recombinant humanized antibody against glypican-3, in patients with advanced hepatocellular carcinoma," Clin Cancer Res., Feb. 15, 2013;19(4):920-8. doi: 10.1158/1078-0432.CCR-12-2616. Epub Jan. 29, 2013.
USPTO Restriction Requirement in U.S. Appl. No. 14/713,416, dated Sep. 9, 2016, 8 pages.
Fish & Richardson P.C., Reply to Restriction Requirement dated Sep. 9, 2016, in U.S. Appl. No. 14/713,416, filed Dec. 9, 2016, 7 pages.
Notice of Allowance for Russian App. Ser. No. 2011115845, dated Oct. 27, 2016 (with English translation), 12 pages.
Bendig, "Humanization of Rodent Monoclonal Antibodies by CDR Grafting," Methods: A Companion to Methods in Enzymology, 1995;8:83-93.
USPTO Non-Final Office Action in U.S. Appl. No. 14/713,416, dated Jan. 19, 2017, 24 pages.
Petrov P.V., "Immunology," M., Meditsina, 1987 p. 70.
Roitt et al., "Immunology," M.: Mir, 2000, pp. 110-111, 151.
Office Action for Russian App. Ser. No. 2011115845, dated Mar. 11, 2015 (with English translation), 8 pages.
USPTO Restriction Requirement in U.S. Appl. No. 11/251,561, dated Dec. 13, 2007, 9 pages.
Fish & Richardson P.C., Response to Restriction Requirement dated Dec. 13, 2007 in U.S. Appl. No. 11/251,561, filed Feb. 12, 2008, 1 page.
USPTO Office Action in U.S. Appl. No. 11/251,561, dated May 14, 2008, 12 pages.
Fish & Richardson P.C., Amendment in Reply to Action dated May 14, 2008 in U.S. Appl. No. 11/251,561, filed Nov. 13, 2008, 8 pages.
USPTO Final Office Action in U.S. Appl. No. 11/251,561, dated Feb. 25, 2009, 13 pages.
Fish & Richardson P.C., Reply to Action dated Feb. 25, 2009 in U.S. Appl. No. 11/251,561, filed Mar. 24, 2010, 4 pages.
Fish & Richardson P.C., Supplemental Amendment in Reply to Action dated Feb. 25, 2009 in U.S. Appl. No. 11/251,561, filed Mar. 26, 2010, 16 pages.
USPTO Non-Final Office Action in U.S. Appl. No. 11/251,561, dated Aug. 4, 2011, 15 pages.
Fish & Richardson P.C., Amendment in Reply to Action dated Aug. 4, 2011 in U.S. Appl. No. 11/251,561, filed Feb. 6, 2012, 24 pages.
USPTO Final Office Action in U.S. Appl. No. 11/251,561, dated May 2, 2012, 21 pages.
USPTO Interview Summary in U.S. Appl. No. 11/251,561, dated Dec. 31, 2012, 3 pages.
Fish & Richardson P.C., Amendment in Reply to Office Action dated May 2, 2012 in U.S. Appl. No. 11/251,561, filed May 22, 2013, 16 pages.
USPTO Final Office Action in U.S. Appl. No. 11/251,561, dated Sep. 25, 2013, 16 pages.
Fish & Richardson P.C., Reply to Final Office Action dated Sep. 25, 2013 in U.S. Appl. No. 11/251,561, filed Feb. 25, 2014, 29 pages.
USPTO Non-Final Office Action in U.S. Appl. No. 11/251,561, dated Apr. 4, 2014, 18 pages.
USPTO Restriction Requirement in U.S. Appl. No. 12/089,957, dated Sep. 1, 2010, 7 pages.
Fish & Richardson P.C., Response to Restriction Requirement dated Sep. 1, 2010 in U.S. Appl. No. 12/089,957, filed Feb. 28, 2011, 1 page.
USPTO Non-Final Office Action in U.S. Appl. No. 12/089,957, dated Mar. 30, 2011, 18 pages.
Fish & Richardson P.C., Amendment in Reply to Office Action dated Mar. 30, 2011 in U.S. Appl. No. 12/089,957, filed Sep. 29, 2011, 12 pages.
USPTO Final Office Action in U.S. Appl. No. 12/089,957, dated Dec. 5, 2011, 14 pages.
Fish & Richardson P.C., Amendment in Reply to Final Office Action dated Dec. 5, 2011 in U.S. Appl. No. 12/089,957, filed Jun. 5, 2012, 11 pages.
USPTO Interview Summary in U.S. Appl. No. 12/089,957, dated Oct. 11, 2012, 3 pages.
USPTO Non-Final Office Action in U.S. Appl. No. 12/089,957, dated Sep. 23, 2013, 10 pages.
Fish & Richardson P.C., Reply to Non-Final Office Action dated Sep. 23, 2013 in U.S. Appl. No. 12/089,957, filed Mar. 3, 2014, 16 pages.
USPTO Final Office Action in U.S. Appl. No. 12/089,957, dated Apr. 16, 2014, 6 pages.
Fish & Richardson P.C., Reply to Final Office Action dated Apr. 16, 2014 in U.S. Appl. No. 12/089,957, filed Mar. 5, 2015, 4 pages.

(56) References Cited

OTHER PUBLICATIONS

USPTO Notice of Allowance in U.S. Appl. No. 12/089,957, dated Apr. 1, 2015, 7 pages.
USPTO Restriction Requirement in U.S. Appl. No. 10/583,795, dated Dec. 18, 2007, 5 pages.
Fish & Richardson P.C., Response to Restriction Requirement dated Dec. 18, 2007 in U.S. Appl. No. 10/583,795, filed Jan. 18, 2008, 19 pages.
USPTO Office Action in U.S. Appl. No. 10/583,795, dated Mar. 27, 2008, 42 pages.
Fish & Richardson P.C., Amendment in Reply to Action dated Mar. 27, 2008 in U.S. Appl. No. 10/583,795, filed Sep. 29, 2008, 46 pages.
USPTO Office Action in U.S. Appl. No. 10/583,795, dated Jan. 7, 2009, 25 pages.
Interview Summary in U.S. Appl. No. 10/583,795, dated Apr. 8, 2009, 2 pages.
Fish & Richardson P.C., Amendment in Reply to Action dated Jan. 7, 2009 in U.S. Appl. No. 10/583,795, filed Apr. 7, 2009, 13 pages.
Interview Summary in U.S. Appl. No. 10/583,795, dated Apr. 20, 2009, 2 pages.
USPTO Office Action in U.S. Appl. No. 10/583,795, dated Jun. 26, 2009, 19 pages.
Fish & Richardson P.C., Amendment in Reply to Action dated Jun. 26, 2009 in U.S. Appl. No. 10/583,795, filed Dec. 24, 2009, 17 pages.
USPTO Notice of Allowance in U.S. Appl. No. 10/583,795, dated Mar. 10, 2010, 16 pages.
USPTO Non-Final Office Action in U.S. Appl. No. 12/797,349, dated Jun. 27, 2012, 27 pages.
Fish & Richardson P.C., Amendment in Reply to Action dated Jun. 27, 2012 in U.S. Appl. No. 12/797,349, filed Dec. 27, 2012, 14 pages.
USPTO Non-Final Office Action in U.S. Appl. No. 12/797,349, dated Apr. 25, 2013, 20 pages.
Fish & Richardson P.C., Amendment in Reply to Office Action dated Apr. 25, 2013 in U.S. Appl. No. 12/797,349, filed Aug. 23, 2013, 9 pages.
USPTO Final Office Action in U.S. Appl. No. 12/797,349, dated Dec. 11, 2013, 6 pages.
Fish & Richardson P.C., Reply to Final Office Action dated Dec. 11, 2013, in U.S. Appl. No. 12/797,349, filed Jan. 9, 2015, 6 pages.
USPTO Restriction Requirement in U.S. Appl. No. 10/570,647, dated Apr. 4, 2008, 6 pages.
USPTO Restriction Requirement in U.S. Appl. No. 11/574,091, dated Dec. 17, 2008, 8 pages.
Fish & Richardson P.C., Response to Restriction Requirement dated Dec. 17, 2008 in U.S. Appl. No. 11/574,091, filed Jun. 16, 2009, 1 page.
USPTO Office Action in U.S. Appl. No. 11/574,091, dated Sep. 2, 2009, 18 pages.
Fish & Richardson P.C., Amendment in Reply to Action dated Sep. 2, 2009 in U.S. Appl. No. 11/574,091, filed Mar. 2, 2010, 7 pages.
USPTO Final Office Action in U.S. Appl. No. 11/574,091, dated May 11, 2010, 16 pages.
Fish & Richardson P.C., Amendment in Reply to Action dated May 11, 2010 in U.S. Appl. No. 11/574,091, filed Aug. 11, 2010, 6 pages.
USPTO Notice of Allowance in U.S. Appl. No. 11/574,091, dated Aug. 31, 2010, 6 pages.
USPTO Office Action in U.S. Appl. No. 11/577,944, dated Apr. 28, 2009, 14 pages.
Fish & Richardson P.C., Amendment in Reply to Office Action dated Apr. 28, 2009 in U.S. Appl. No. 11/577,944, filed Oct. 27, 2009, 15 pages.
USPTO Final Office Action in U.S. Appl. No. 11/577,944, dated Jan. 20, 2010, 47 pages.
Fish & Richardson P.C., Amendment in Reply to Office Action dated Jan. 20, 2010 in U.S. Appl. No. 11/577,944, filed Apr. 29, 2010, 6 pages.
USPTO Interview Summary in U.S. Appl. No. 11/577,944, dated May 3, 2010, 3 pages.
USPTO Non-Final Office Action in U.S. Appl. No. 11/577,944, dated May 21, 2010, 16 pages.
Fish & Richardson P.C., Amendment in Reply to Office Action dated May 21, 2010 in U.S. Appl. No. 11/577,944, filed Jun. 9, 2010, 5 pages.
USPTO Notice of Allowance in U.S. Appl. No. 11/577,944, dated Aug. 26, 2010, 6 pages.
USPTO Restriction Requirement in U.S. Appl. No. 12/852,950, dated Aug. 21, 2012, 7 pages.
Fish & Richardson P.C., Response to Restriction Requirement dated Aug. 21, 2012 in U.S. Appl. No. 12/852,950, filed Feb. 5, 2013, 1 page.
USPTO Restriction Requirement in U.S. Appl. No. 12/852,950, dated Feb. 25, 2013, 7 pages.
Fish & Richardson P.C., Amendment and Reply to Restriction Requirement dated Feb. 25, 2013 in U.S. Appl. No. 12/852,950, filed Jun. 25, 2013, 14 pages.
USPTO Non-Final Office Action in U.S. Appl. No. 12/852,950, dated Oct. 4, 2013, 34 pages.
Fish & Richardson P.C., Amendment in Reply to Action dated Oct. 4, 2013 in U.S. Appl. No. 12/852,950, filed Apr. 3, 2014, 49 pages.
USPTO Final Office Action in U.S. Appl. No. 12/852,950, dated Jul. 16, 2014, 38 pages.
Fish & Richardson P.C., Amendment in Reply to Action dated Jul. 16, 2014 in U.S. Appl. No. 12/852,950, filed Mar. 16, 2015, 21 pages.
USPTO Restriction Requirement in U.S. Appl. No. 10/526,741, dated Mar. 27, 2006, 5 pages.
Davidson, Davidson & Kappel, LLC, Response to Restriction Requirement dated Mar. 27, 2006 in U.S. Appl. No. 10/526,741, filed Apr. 25, 2006, 6 pages.
USPTO Office Action in U.S. Appl. No. 10/526,741, dated Jun. 14, 2006, 40 pages.
Davidson, Davidson & Kappel, LLC, Amendment in Reply to Office Action dated Jun. 14, 2006 in U.S. Appl. No. 10/526,741, filed Dec. 12, 2006, 18 pages.
USPTO Final Office Action in U.S. Appl. No. 10/526,741, dated Mar. 9, 2007, 17 pages.
Davidson, Davidson & Kappel, LLC, Amendment in Reply to Office Action dated Mar. 9, 2007 in U.S. Appl. No. 10/526,741, filed Jul. 9, 2007, 9 pages.
USPTO Advisory Action in U.S. Appl. No. 10/526,741, dated Aug. 14, 2007, 3 pages.
Davidson, Davidson & Kappel, LLC, Amendment in Reply to Action dated Aug. 14, 2007 in U.S. Appl. No. 10/526,741, filed Sep. 6, 2007, 9 pages.
USPTO Office Action in U.S. Appl. No. 10/526,741, dated Nov. 21, 2007, 17 pages.
Davidson, Davidson & Kappel, LLC, Amendment in Reply to Action dated Nov. 21, 2007 in U.S. Appl. No. 10/526,741, filed Mar. 20, 2008, 10 pages.
USPTO Final Office Action in U.S. Appl. No. 10/526,741, dated Jul. 9, 2008, 11 pages.
Davidson, Davidson & Kappel, LLC, Amendment in Reply to Office Action dated Jul. 9, 2008 in U.S. Appl. No. 10/526,741, filed Jan. 5, 2009, 113 pages.
USPTO Advisory Action in U.S. Appl. No. 10/526,741, dated Jan. 21, 2009, 4 pages.
USPTO Office Action in U.S. Appl. No. 10/526,741, dated Sep. 1, 2009, 15 pages.
Davidson, Davidson & Kappel, LLC, Amendment in Reply to Office Action dated Sep. 1, 2009 in U.S. Appl. No. 10/526,741, filed Feb. 24, 2010, 10 pages.
USPTO Office Action in U.S. Appl. No. 10/481,524, dated Apr. 3, 2006, 23 pages.
Davidson, Davidson & Kappel, LLC, Amendment in Reply to Office Action dated Apr. 3, 2006 in U.S. Appl. No. 10/481,524, filed Aug. 31, 2006, 9 pages.
USPTO Interview Summary in U.S. Appl. No. 10/481,524, dated Sep. 6, 2006, 3 pages.

(56) References Cited

OTHER PUBLICATIONS

USPTO Restriction Requirement in U.S. Appl. No. 10/481,524, dated Jan. 5, 2007, 4 pages.
USPTO Office Communication in U.S. Appl. No. 10/481,524, dated Jan. 23, 2007, 2 pages.
USPTO Restriction Requirement in U.S. Appl. No. 11/702,780, dated Jul. 24, 2007, 5 pages.
Davidson, Davidson & Kappel, LLC, Response to Restriction Requirement dated Jul. 24, 2007 in U.S. Appl. No. 11/702,780, filed Aug. 22, 2007, 4 pages.
USPTO Office Action in U.S. Appl. No. 11/702,780, dated Nov. 16, 2007, 9 pages.
USPTO Interview Summary in U.S. Appl. No. 11/702,780, dated Dec. 14, 2007, 4 pages.
Davidson, Davidson & Kappel, LLC, Amendment in Reply to Office Action dated Nov. 16, 2007 in U.S. Appl. No. 11/702,780, filed May 16, 2008, 11 pages.
USPTO Office Action in U.S. Appl. No. 11/702,780, dated Sep. 3, 2008, 9 pages.
Davidson, Davidson & Kappel, LLC, Amendment in Reply to Office Action dated Sep. 3, 2008 in U.S. Appl. No. 11/702,780, filed Dec. 29, 2008, 6 pages.
USPTO Advisory Action in U.S. Appl. No. 11/702,780, dated Jan. 13, 2009, 4 pages.
USPTO Office Action in U.S. Appl. No. 11/702,780, dated Apr. 2, 2009, 7 pages.
Davidson, Davidson & Kappel, LLC, Amendment in Reply to Office Action dated Apr. 2, 2009 in U.S. Appl. No. 11/702,780, filed Sep. 30, 2009, 215 pages.
USPTO Notice of Allowance in U.S. Appl. No. 11/702,780, dated Jan. 26, 2010, 5 pages.
Abe et al., "MatrixeyeTM Portable 3D Ultrasonic Inspection System," Toshiba Rev., 60:48-51, English abstract (2005).
Arii et al., "Characteristics of recurrent hepatocellular carcinoma in Japan and our surgical experience," J. Hepatobiliary Pancrea. Surg. 8:397-403 (2001).
Baneyx, "Recombinant protein expression in *Escherichia coli*," Curr. Opin. Biotechnol., 10:411-421 (1999).
Bendayan, "Possibilities of False Immunocytochemical Results Generated by the Use of Monoclonal Antibodies: The Example of the Anti-Proinsulin Antibody," J. Histochem. Cytochem., 43(9):881-886 (1995).
Bost et al., "Antibodies Against a Peptide Sequence within the HIV Envelope Protein Crossreacts with Human Interleukin-2," Immunol. Invest., 17:577-586 (1988).
Brorson et al., "Mutational Analysis of Avidity and Fine Specificity of Anti-Levan Antibodies," J. Immunol., 163:6694-6701 (1999).
Brummell et al., "Probing the combining site of an anti-carbohydrate antibody by saturation-mutagenesis: role of the heavy-chain CDR3 residues," Biochemistry, 32:1180-87 (1993).
Budhu et al., "The Molecular Signature of Metastases of Human Hepatocellular Carcinoma," Oncology, 69(suppl 1):23-27 (2005).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-38 (1990).
Burks et al., "In vitro scanning saturation mutagenesis of an antibody binding pocket," Proc. Natl. Acad. Sci. USA, 94:412-417 (1997).
Caldas et al., "Humanization of the anti-CD18 antibody 6.7: an unexpected effect of a framework residue in binding to antigen," Mol. Immunol., 39(15):941-52 (2003).
Cappuro et al., "Overexpression of Glypican-3 in Human Hepatocellular Carcinomas Determined by Immunohistochemistry Using a Monocolonal Antibody," Proceedings of the Annual Meeting of the American Association for Cancer Research, 93rd Annual Meeting, Apr. 6-10, 2002, 43:219 Abstract #1097 (2002).

Capurro et al. "Glypican-3: A novel serum and histochemical marker for hepatocellular carcinoma," Gastroenterology, 125:89-97 (2003).
Carter, "Improving the efficacy of antibody-based cancer therapies," Nat. Rev. Cancer, 1:118-129 (2001).
Carter et al., "Humanization of an anti-p185HER2 antibody for human cancer therapy," Proc. Natl. Acad. Sci. U.S.A., 89:4285-4289 (1992).
Casset et al., "A peptide mimetic of an anti-CD4 monoclonal antibody by rational design," Biochem. Biophys. Res. Commun., 307:198-205 (2003).
Chen et al., "Selection and Analysis of an Optimized Anti-VEGF Antibody: Crystal Structure of an Affinity-Matured Fab in Complex with Antigen," J. Mol. Biol., 293:865-881 (1999).
Chien et al., "Significant structural and functional change of an antigen-binding site by a distant amino acid substitution: proposal of a structural mechanism," Proc. Natl. Acad. Sci. USA, 86(14):5532-5536 (1989).
Colman, "Effects of amino acid sequence changes on antibody-antigen interactions," Res. Immunol., 145:33-36 (1994).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol., 169:3076-84 (2002).
Declaration of Pamela J. Bjorkman under 37 C.F.R. §1.132, dated Jan. 17, 2011, 14 pages.
Dennis, "Cancer: Off by a whisker," Nature, 442:739-741 (2006).
Dipiro et al., "Lesson 2: Basic Pharmacokinetics," Concept in Clinical Pharmacokinetics, Fifth Edition, American Society of Health-System Pharmacists, pp. 19-28 (2010).
Dufner et al., "Harnessing phage and ribosome display for antibody optimization," Trends Biotechnol., 24:523-529 (2006).
Filmus, "Glypicans in Growth Control and Cancer," Glycobiology, 11(3):19R-23R (2001).
Ghetie et al., "Multiple Roles for the Major Histocompatibility Complex Class I-Related Receptor FcRn," Annu. Rev. Immunol., 18:739-766 (2000).
Gonzalez et al. "OCI-5/GPC3, A Glypican Encoded by a Gene That is Mutated in the Simpson-Golabi-Behmel Overgrowth Syndrome, Induces Apoptosis in a Cell Line-Specific Manner, " J. Cell Biol., 141:1407-14 (1998).
Greenspan et al., "Defining epitopes: It's not as easy as it seems," Nat. Biotechnol., 17:936-7 (1999).
Gura, "Systems for Identifying New Drugs Are Often Faulty," Science, 278:1041-42 (1997).
Hinton et al,. "Engineered Human IgG Antibodies with Longer Serum Half-lives in Primates," J. Biol. Chem., 279:6213-16 (2004).
Hippo et al., "Identification of Soluble $NH_2$-Terminal Fragment of Glypican-3 as a Serological Marker for Early-Stage Hepatocellular Carcinoma," Cancer Res., 64:2418-23 (2004).
Ho et al., "Glypican-3: a new target for cancer immunotherapy," Eur. J. Cancer, 47:333-338 (2011).
Holm et al., "Functional mapping and single chain construction of the anti-cytokeratin 8 monoclonal antibody TS1," Mol. Immunol., 44:1075-84 (2007).
Houdebine, "Production of pharmaceutical proteins from transgenic animals," J. Biotechnol., 34:269-287 (1994).
Huber, "Structure and Function of the Human Glypican 3 Gene," Washington University, Division of Biology and Biomedical Sciences Program in Molecular Genetics, St. Louis, Missouri (Dec. 1998).
Ishiguro et al., "Anti-glypican 3 antibody as a potential antitumor agent for human liver cancer," Cancer Res., 68(23):9832-8 (2008).
Jang et al., "The structural basis for DNA binding by an anti-DNA autoantibody," Mol. Immunol., 35:1207-17 (1998).
Jiang et al., "Recurrence or metastasis of HCC: predictors, early detection and experimental antiangiogenic therapy," World J. Gastroenterol., 6:61-65 (2000).
Johnson et al., "The Kabat database and a bioinformatics example," Methods Mol. Biol., 248:11-25 (2004).
Kappel et al., "Regulating gene expression in transgenic animals" Curr. Opin. Biotechnol., 3:548-553 (1992).

(56) References Cited

OTHER PUBLICATIONS

Kim et al., "Mapping the site on human IgG for binding of the MHC class I-related receptor, FcRn," Eur. J. Immunol., 29:2819-25 (1999).
Kobayashi et al., "Tryptophan H33 plays an important role in pyrimidine (6-4) pyrimidone photoproduct binding by a high-affinity antibody," Protein Eng., 12:879-884 (1999).
Kumar et al., "Molecular Cloning and Expression of the Fabs of Human Autoantibodies in *Escherichia coli*," J. Biol. Chem., 275(45):35129-36 (2000).
Lage et al. "Cloning and Characterization of Human cDNAs Encoding a Protein with High Homology to Rat Intestinal Development Protein OCI-5," Gene, 188:151-156 (1997).
Lage et al. "Expression of a Glypican-Related 62-kDa Antigen is Decreased in Hepatocellular Carcinoma in Correspondence to the Grade of Tumor Differentiation," Virchows Arch, 438:567-573 (2001).
Lazar et al., "Transforming Growth Factor alpha: Mutation of Aspartic Acid 47 and Leucine 48 Results in Different Biological Activities," Mol. Cell. Biol., 8:1247-52 (1988).
Lund et al., "Multiple interactions of IgG with its core oligosaccharide can modulate recognition by complement and human Fc gamma receptor I and influence the synthesis of its oligosaccharide chains," J. Immunol., 157:4963-69 (1996).
MacCallum et al., "Antibody-antigen Interactions: Contact Analysis and Binding Site Topography," J. Mol. Biol., 262:732-745 (1996).
Man et al., "Upregulation of Glypican-3 Expression in Hepatocellular Carcinoma but Downregulation in Cholangiocarcinoma Indicates its Differential Diagnosis Value in Primary Liver Cancers," Liver International, 25:962-966 (2005).
Martin et al., "Crystal Structure at 2.8 A of an FcRn/Heterodimeric Fc Complex: Mechanism of pH-Dependent Binding," Molecular Cell, 7:867-877 (2001).
Medesan et al., "Delineation of the Amino Acid Residues Involved in Transcytosis and Catabolism of Mouse IgG1," J. Immunol., 158:2211-17 (1997).
Midorikawa et al. "Glypican-3, Overexpressed in Hepatocellular Carcinoma, Modulates FGF2 and BMP-7 Signaling," Int. J. Cancer, 103:445-465 (2003).
MSNBC News Service, "Mixed results on new cancer drug," 4 pages (2000).
Nakano et al., "Anti-glypican 3 antibodies cause ADCC against human hepatocellular carcinoma cells," Biochem. Biophys. Res. Comm., 378:279-284 (2009).
Nakatsura et al., "Glypican-3, overexpressed specifically in human hepatocellular carcinoma, is a novel tumor marker," Biochem. Biophys. Res. Commun., 306:16-25 (2003).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Res., 64:2127-33 (2004).
Noda et al., "Relationship between elevated FX expression and increased production of GDP-L-fucose, a common donor substrate for fucosylation in human hepatocellular carcinoma and hepatoma cell lines," Cancer Res., 63:6282-6289 (2003).
Ohno et al., "Antigen-binding specificities of antibodies are primarily determined by seven residues of VH," Proc. Natl. Acad. Sci. U.S.A., 82:2945-2945 (1985).
Panka et al., Variable region framework differences result in decreased or increased affinity of variant anti-digoxin antibodies, Proc. Natl. Acad. Sci. U.S.A., 85:3080-4 (1988).
Pannetier et al., "The sizes of the CDR3 hypervariable regions of the murine T-cell receptor beta chains vary as a function of the recombined germ-line segments," Proc. Natl. Acad. Sci. U.S.A., 90:4319-4323 (1993).
Paul, "Structure and function of immunoglobulins," Fundamental Immunology, Third Edition, 292-295 (1993).
Pilia et al. "Mutations in GPC3, A Glypican Gene, Cause the Simpson-Golabi-Behmel Overgrowth Syndrome," Nature Genetics, 12:241-247 (1996).
Portolano et al., "Lack of promiscuity in autoantigen-specific H and L chain combinations as revealed by human H and L chain 'roulette'," J. Immunol., 150:880-887 (1993).
Presta, LG, "Engineering Antibodies for Therapy," Curr. Pharm. Biotechnol., 3:237-356 (2002).
Raghavan et al., "Fc Receptors and their Interactions with Immunoglobulins," Annu. Rev. Cell Dev. Biol., 12:181-220 (1996).
Roitt et al., "Immunology," Moscow, 102, 106-107 (2000) (English translation).
Roskams et al., "Heparan sulphate proteoglycan expression in human primary liver tumours," J. Pathol., 185:290-297 (1998).
Rudikoff et al., "Single amino acid substitution altering antigen-binding specificity," Proc. Natl. Acad. Sci. USA, 79:1979-83 (1982).
Sabit et al., "Enhanced expression of basement-membrane-type heparan sulfate proteoglycan in tumor fibro-myxoid stroma of intrahepatic cholangiocarcinoma," Pathol. Int., 51:248-256 (2001).
Seaver, "Monoclonal Antibodies in Industry: More Difficult Than Originally Thought," Genetic Engineering, 14(14):pp. 10 and 21 (1994).
Shields et al., "Lack of Fucose on Human IgG1 N-Linked Oligosaccharide Improves Binding to Human Fc gamma RIII and Antibody-dependent Cellular Toxicity," J. Biol. Chem., 277:26733-40 (2002).
Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," J. Biol. Chem., 278:3466-73 (2003).
Shuo et al., "The Antitumor Effects of Anti-CD71 Mouse/Human Chimeric Antibody in vitro," J Huazhong Univ Sci Tech (Health Sci), 32(1):13 (Feb. 2003) (including English abstract).
Smith-Gill et al., "Contributions of immunoglobulin heavy and light chains to antibody specificity for lysozyme and two haptens," J. Immunol., 139:4135-44 (1987).
Soderlind et al., "The immune diversity in a test tube—non-immunised antibody libraries and functional variability in defined protein scaffolds," Comb. Chem. High Throughput Screen., 4:409-416 (2001).
Song et al., "Light Chain of Natural Antibody Plays a Dominant Role in Protein Antigen Binding," Biochem. Biophys. Res. Commun., 268:390-394 (2000).
Steplewski et al., Biological activity of human-mouse IgG1, IgG2, IgG3, and IgG4 chimeric monoclonal antibodies with antitumor specificity, Proc. Natl. Acad. Sci. USA, 85:4852-56 (1988).
Sung et al. "Glypican-3 is overexpressed in human hepatocellular carcinoma," Cancer Science, 94:259-262 (2003).
Tamura et al., "Structural correlates of an anticarcinoma antibody: identification of specificity-determining residues (SDRs) and development of a minimally immunogenic antibody variant by retention of SDRs only," J. Immunol., 164(3):1432-1441 (2000).
Tang et al., "Metastatic human hepatocellular carcinoma models in nude mice and cell line with metastatic potential," World J. Gastroenterol., 7:597-601 (2001).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Voskoglou-Nomikos et al., "Clinical Predictive Value of the in Vitro Cell Line, Human Xenograft, and Mouse Allograft Preclinical Cancer Models," Clin. Cancer Res., 9:4227-39 (2003).
Wall, "Transgenic Livestock: Progress and Prospects for the Future," Theriogenology, 45:57-68 (1996).
Wang et al., "Monoclonal Antibody Pharmacokinetics and Pharmacodynamics," Clinical Phaimacology & Therapeutics, 84(5):548-558 (2008).
Wichert et al., "Glypican-3 is involved in cellular protection against mitoxantrone in gastric carcinoma cells," Oncogene, 23:945-955 (2004).
Winkler et al., "Changing the antigen binding specificity by single point mutations of an anti-p24 (HIV-1) antibody," J. Immunol., 165(8):4505-4514 (2000).
Winter et al., "Humanized antibodies," Immunol. Today, 14(6):243-6 (1993).
Wu et al., "Length distribution of CDRH3 in antibodies," Proteins, 16:1-7 (1993).

(56) References Cited

OTHER PUBLICATIONS

Wu et al., "Humanization of a Murine Monoclonal Antibody by Simultaneous Optimization of Framework and CDR Residues," J. Mol. Biol., 294:151-162 (1999).
Yamaguchi et al., "Current Status and Future Perspective of Biotherapy for Cancer," Biotherapy, 13:747-753 (1999) (English summary included).
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol. Bioeng., 87:614-622 (2004).
International Search Report and Written Opinion for App. Ser. No. PCT/US2006/039682 dated Apr. 13, 2007, 13 pages.
International Search Report for App. Ser. No. PCT/JP2005/013103, dated Oct. 25, 2005, 1 page.
International Preliminary Report on Patentability for App. Ser. No. PCT/JP2005/013103, dated Jan. 7, 2009, 4 pages.
European Search Report for App. Ser. No. EP 05 76 0156, dated Oct. 1, 2007, 15 pages.
Partial European Search Report for App. Ser. No. 10 00 3424 dated Jun. 7, 2010, 11 pages.
International Search Report for App. Ser. No. PCT/JP2004/013183, dated Nov. 30, 2004, 4 pages.
International Preliminary Report on Patentability for App. Ser. No. PCT/JP2004/013183, dated Sep. 1, 2005, 17 pages.
European Search Report for App. Ser. No. EP 04 77 2 922, dated Jun. 14, 2007, 2 pages.
International Search Report for App. Ser. No. PCT/JP2005/015607, dated Oct. 24, 2005, 3 pages.
European Search Report for App. Ser. No. EP 05 78 0979, dated Nov. 10, 2008, 5 pages.
International Search Report for App. Ser. No. PCT/JP2005/020057, dated Jan. 24, 2006, 2 pages.
European Search Report for App. Ser. No. EP 05 80 0031, dated Jul. 31, 2009, 9 pages.
Search Report and Written Opinion for App. Ser. No. SG 200703074-5, dated Jul. 21, 2008, 9 pages.
Office Action for Canadian App. Ser. No. 2,544,692, dated Aug. 1, 2011, 6 pages.
Office Action for Canadian App. Ser. No. 2,544,692, dated Sep. 4, 2012, 3 pages.
Office Action for Canadian App. Ser. No. 2,585,196, dated May 29, 2012, 3 pages.
Office Action for Chinese App. Ser. No. 201210178007.3, dated Sep. 29, 2013, 8 pages.
Office Action for Taiwanese App. Ser. No. 094137496, dated Dec. 31, 2010, 8 pages.
Office Action for Costa Rica App. Ser. No. 9151, dated Feb. 18, 2013, 15 pages.
European Search Report for App Ser. No. EP 13 86 4465, dated Jun. 10, 2016, 8 pages.
USPTO Office Action in U.S. Appl. No. 14/629,967, dated Mar. 28, 2016, 18 pages.
USPTO Office Action in U.S. Appl. No. 12/584,728 dated Mar. 30, 2016, 33 pages.
Oral Hearing for Indian App. Ser. No. 1929/CHENP/2006, dated Jul. 19, 2017, 3 pages.
ClinicalTrials.gov, View of NCT00746317, dated Nov. 16, 2010, 4 pages.
Llovet et al., "A molecular signature to discriminate dysplastic nodules from early hepatocellular carcinoma in HCV cirrhosis," Gastroenterology, Dec. 2006;131(6):1758-67. Epub Sep. 19, 2006.
USPTO Office Action in U.S. Appl. No. 14/629,967, dated Mar. 24, 2017, 13 pages.
Office Action for Indian App. Ser. No. 6501/CHENP/2010, dated Apr. 12, 2017, 7 pages.
USPTO Office Action in U.S. Appl. No. 14/441,551, dated Jan. 9, 2017, 15 pages.
Fish & Richardson P.C., Reply to Non-Final Office Action dated Jan. 19, 2017, in U.S. Appl. No. 14/713,416, filed Jun. 19, 2017, 279 pages.
USPTO Final Office Action in U.S. Appl. No. 14/713,416, dated Aug. 15, 2017, 12 pages.
Notice of Allowance for Chinese App. Ser. No. 201210154813.7, dated May 12, 2017 (with English translation), 6 pages.
Abou-Alfa et al., "Randomized phase II placebo controlled study of codrituzumab in previously treated patients with advanced hepatocellular carcinoma," J Hepatol., Apr. 13, 2016; 65(2):289-95.
Chia-Jui et al., "Randomized phase II trial of intravenous RO5137382/GC33 at 1600 mg every other week and placebo in previously treated patients with unresectable advanced hepatocellular carcinoma (HCC; NCT01507168)," J. Clinical Oncology, May 20, 2014; 32(15):4102.
Fischer et al., "The anti-lymphoma effect of antibody-mediated immunotherapy is based on an increased degranulation of peripheral blood natural killer (NK) cells," Exp Hematol., 2006;34(6):753-759.
Harlow et al., "Antibodies, a Laboratory Manual," Cold Spring Harbor Laboratory Press, 1988; 141-142.
Hirotake et al., "Histopathological analyses of the antitumor activity of anti-glypican-3 antibody (GC33) in human liver cancer xenograft models: The contribution of macrophages," Cancer Biol Ther., May 1, 2009;8(10):930-8.
Ofuji et al., "Vaccine Therapy for Hepatic Cancer," Consensus of Cancer Therapy, 2013;12(2):114-116 (with English translation).
Sawada et al., "Phase I Trial of a Glypican-3-Derived Peptide Vaccine for Advanced Hepatocellular Carcinoma: Immunologic Evidence and Potential for Improving Overall Survival," Clin Cancer Res., May 10, 2012;18(13):3686-3696.
Semenova, "Monitoring of Treatment Efficacy and Detection of Recurrences Using Biomarkers," Practical Oncology, 2011;12(4):171-177 (with English translation).
Final Office Action in U.S. Appl. No. 14/441,551, dated Oct. 16, 2017, 28 pages.
Office Action in U.S. Appl. No. 15/288,508, dated Jan. 9, 2018, 52 pages.
Office Action for Chinese App. Ser. No. 201480071111.X, dated Oct. 16, 2017, 4 pages.
Search Report for European App. Ser. No. 15789676.2, dated Nov. 28, 2017, 10 pages.
Hearing Notice for Indian App. Ser. No. 2357/CHENP/2010, dated Jan. 29, 2018, 4 pages.
Office Action for Norway App. Ser. No. 20063539, dated Feb. 8, 2018, 6 pages.
Office Action for Russian App. Ser. No. 2015129697, dated Dec. 7, 2017, 7 pages.
Written Opinion for Singapore App. Ser. No. 11201609014T, dated Oct. 16, 2017, 8 pages.
Fish & Richardson P.C., Appeal Brief in U.S. Appl. No. 14/713,416, filed Mar. 16, 2018, 8 pages.

\* cited by examiner

ANTI-GLYPICAN-3 ANTIBODY

CROSS REFERENCE TO RELATED APPLICATION

This application is a continuation claiming priority to U.S. application Ser. No. 11/251,561, filed on Oct. 14, 2005.

TECHNICAL FIELD

The present invention relates to an anti-glypican-3 antibody. Specifically, the present invention relates to an anti-glypican-3 antibody which has modifications in the amino acid sequence of the Fc region and exhibits enhanced ADCC activity.

BACKGROUND

Glypican-3 (GPC3) is one of a heparan sulfate proteoglycan family existing on the surface of cells, and it is suggested that GPC3 may participate in cell division in development and in growth of cancer cells, but its function is not as yet well clarified.

It has been found that a certain antibody binding to GPC3 has a cell growth-inhibiting effect through its ADCC (antibody-dependent cytotoxicity) activity and CDC (complement-dependent cytotoxicity) (WO2003/000883, hereby incorporated by reference in its entirety).

In the case where an anticancer agent utilizing the cytotoxicity activity of an antibody is developed, it is desirable that the antibody to be used has enhanced ADCC activity. Thus, an anti-GPC3 antibody having enhanced cytotoxicity activity is desired for the GPC3-recognizing antibody.

An object of the invention is to provide an anti-GPC3 antibody having enhanced cytotoxicity as compared with conventional antibodies.

SUMMARY

It was found that an anti-glypican-3 antibody with enhanced ADCC activity may be obtained by modifying the amino acid sequence in the Fc region of the antibody.

In one aspect, the present invention provides an anti-glypican-3 antibody comprising one or more amino acid substitutions introduced in the Fc region.

In another aspect, the present invention provides an anti-glypican-3 antibody in which one or more of the amino acid residues at the positions 239, 298, 326, 330 and 332 in the Fc region are substituted with other amino acid residues.

In another aspect, the present invention provides an anti-glypican-3 antibody selected from the group consisting of:

(a) an anti-glypican-3 antibody in which the amino acid residue at the position 332 of the Fc region is substituted with another amino acid residue;

(b) an anti-glypican-3 antibody in which the amino acid residues at the positions 239, 330 and 332 of the Fc region are substituted with other amino acid residues;

(c) an anti-glypican-3 antibody in which the amino acid residues at the positions 239, 298 and 332 of the Fc region are substituted with other amino acid residues;

(d) an anti-glypican-3 antibody in which the amino acid residues at the positions 239, 326 and 332 of the Fc region are substituted with other amino acid residues;

(e) an anti-glypican-3 antibody in which the amino acid residues at the positions 239, 298, 326 and 332 of the Fc region are substituted with other amino acid residues.

In another aspect, the present invention provides an anti-glypican-3 antibody selected from the group consisting of:

(a) an anti-glypican-3 antibody having glutamic acid at the position 332 of the Fc region;

(b) an anti-glypican-3 antibody having aspartic acid at the position 239, leucine at the position 330, and glutamic acid at the position 332 of the Fc region;

(c) an anti-glypican-3 antibody having aspartic acid at the position 239, alanine at the position 298, and glutamic acid at the position 332 of the Fc region;

(d) an anti-glypican-3 antibody having aspartic acid at the position 239, threonine at the position 326, and glutamic acid at the position 332 of the Fc region;

(e) an anti-glypican-3 antibody having aspartic acid at the position 239, alanine at the position 298, glutamic acid at the position 326, and glutamic acid at the position 332 of the Fc region.

In another aspect, the present invention provides an anti-glypican-3 antibody selected from the group consisting of:

(a) an anti-glypican-3 antibody in which the amino acid residue at the position 332 of the Fc region is substituted with glutamic acid;

(b) an anti-glypican-3 antibody in which the amino acid residues at the positions 239, 330 and 332 of the Fc region are substituted with aspartic acid, leucine, and glutamic acid, respectively;

(c) an anti-glypican-3 antibody in which the amino acid residues at the positions 239, 298 and 332 of the Fc region are substituted with aspartic acid, alanine, and glutamic acid, respectively;

(d) an anti-glypican-3 antibody in which the amino acid residues at the positions 239, 326 and 332 of the Fc region are substituted with aspartic acid, threonine, and glutamic acid, respectively;

(e) an anti-glypican-3 antibody in which the amino acid residues at the positions 239, 298, 326 and 332 of the Fc region are substituted with aspartic acid, alanine, glutamic acid, and glutamic acid, respectively.

In another aspect, the present invention provides an anticancer agent comprising the anti-glypican-3 antibody of the invention and a pharmaceutically acceptable carrier, as well as a method of treating a patient with cancer comprising administering to the patient the anticancer agent of the invention.

In another aspect, the present invention provides a method for producing an anti-glypican-3 antibody with enhanced cytotoxicity comprising:

(i) culturing a host cell engineered to express a polynucleotide coding for an anti-glypican-3 antibody in which one or more of the amino acid residues at the positions 239, 298, 326, 330 and 332 of the Fc region are substituted by other amino acid residues; and (ii) isolating the antibody from the culture.

In another aspect, the present invention provides a method for producing an anti-glypican-3 antibody with enhanced cytotoxicity comprising:

(i) culturing a host cell engineered to express a polynucleotide coding for an anti-glypican-3 antibody selected from the group consisting of:

(a) an anti-glypican-3 antibody in which the amino acid residue at the position 332 of the Fc region is substituted with another amino acid residue;

(b) an anti-glypican-3 antibody in which the amino acid residues at the positions 239, 330 and 332 of the Fc region are substituted with other amino acid residues;

(c) an anti-glypican-3 antibody in which the amino acid residues at the positions 239, 298 and 332 of the Fc region are substituted with other amino acid residues;

(d) an anti-glypican-3 antibody in which the amino acid residues at the positions 239, 326 and 332 of the Fc region are substituted with other amino acid residues;

(e) an anti-glypican-3 antibody in which the amino acid residues at the positions 239, 298, 326 and 332 of the Fc region are substituted with other amino acid residues; and (ii) isolating the antibody from the culture.

In another aspect, the present invention provides a method for producing an anti-glypican-3 antibody with enhanced cytotoxicity comprising:

(i) culturing a host cell engineered to express a polynucleotide coding for an anti-glypican-3 antibody selected from the group consisting of:

(a) an anti-glypican-3 antibody having glutamic acid at the position 332 of the Fc region;

(b) an anti-glypican-3 antibody having aspartic acid at the position 239, leucine at the position 330, and glutamic acid at the position 332 of the Fc region;

(c) an anti-glypican-3 antibody aspartic acid at the position 239, alanine at the position 298, and glutamic acid at the position 332 of the Fc region;

(d) an anti-glypican-3 antibody having aspartic acid at the position 239, threonine at the position 326, and glutamic acid at the position 332 of the Fc region;

(e) an anti-glypican-3 antibody having aspartic acid at the position 239, alanine at the position 298, glutamic acid at the position 326, and glutamic acid at the position 332 of the Fc region; and (ii) isolating the antibody from the culture.

In still another aspect, the present invention provides an anti-glypican-3 antibody selected from the group consisting of:

(a) an anti-glypican-3 antibody having the CH2-CH3 domain comprising the amino acid sequence set forth in SEQ ID NO: 34;

(b) an anti-glypican-3 antibody having the CH2-CH3 domain comprising the amino acid sequence set forth in SEQ ID NO: 35;

(c) an anti-glypican-3 antibody having the CH2-CH3 domain comprising the amino acid sequence set forth in SEQ ID NO: 36;

(d) an anti-glypican-3 antibody having the CH2-CH3 domain comprising the amino acid sequence set forth in SEQ ID NO: 37; and (e) an anti-glypican-3 antibody having the CH2-CH3 domain comprising the amino acid sequence set forth in SEQ ID NO: 38.

DETAILED DESCRIPTION

Figure 1:
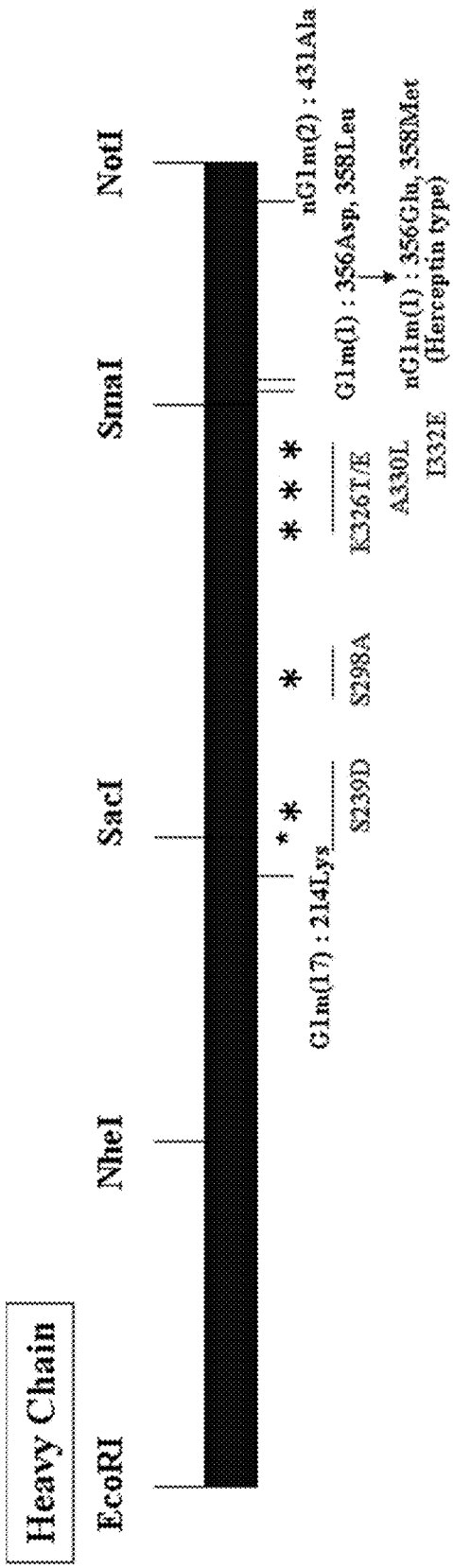
FIG. 1 shows the scheme for preparing the Fc-modified humanized anti-glypican-3 antibody of the invention.

The present invention provides an antibody having modifications in the Fc region. FIG. 1 shows the structure and preparation scheme of the Fc-modified humanized anti-glypican-3 antibody of the invention.

In general, the antibody is a heterotetramer of about 150,000 daltons, and comprises two same light (L) chains and two same heavy (H) chains. Each light chain is bound to the heavy chain via one covalent disulfide bond, and the number of the disulfide bonds between the heavy chains varies depending on the isotype of antibody. The heavy chain and the light chain each have intra-chain disulfide bridges at certain intervals. Each heavy chain has a variable domain (VH) at one terminal thereof, and has many constant domains linked thereto. Each light chain has a variable domain (VL) at one terminal thereof and has a constant region at the other terminal thereof. The constant region of the light chain is in parallel to the first constant region of the heavy chain, and the variable region of the light chain is in parallel to the variable region of the heavy chain. It is believed that specific amino acid residues form an interface of the variable domain of the light chain and the heavy chain (Clothia et al., J. Mol. Biol., 186:651-666 (1985); Novotny and Haber, Proc. Natl. Acad. Sci. USA 82:4592-4596 (1985), all hereby incorporated by reference in its entirety).

The light chain of a vertebrate-derived antibody may be classified into two different types, referred to as kappa (κ) and lambda (λ), based on the amino acid sequence of the constant region thereof. In addition, the antibody may be classified into different classes based on the amino acid sequence of the constant domain of the heavy chain thereof. The antibody includes at least five main classes: IgA, IgD, IgE, IgG and IgM, and some of them may be classified into subclasses (isotypes), e.g., IgG-1, IgG-2, IgG-3 and IgG-4; IgA-1 and IgA-2. The heavy chain constant domains of different classes are referred to as α, δ, ε, γ and μ. The subunit structure and the three-dimensional structure of immunoglobulin of each class are known in the art. It is also known that there exist allotypes in the sequence of the Fc region of IgG-1, for example, G1m(1), nG1m(1), G1m(2), G1m(3), nG1m(17), etc. (M. S. Schanfield and E. van Loghem, "Human Immunoglobulin Allotypes" Handbook of Experimental Immunology, Vol. 3, ch94, pp 1-18, Blackwell Scientific Publishers. Oxford, U.K. 1986, 4th Edition, hereby incorporated by reference in its entirety).

Fc region means a region of an Fc fragment of an antibody molecule, comprising a part of hinge, CH2 and CH3 domains and having a molecular weight of about 50,000. A human IgG heavy chain Fc region is from the 225th threonine to the C-terminal, in the case that the molecule is digested with papain (Burton, D. R. 1985. Immunoglobulin G: functional sites. Mol. Immunol. 22:161-206, hereby incorporated by reference in its entirety).

The numbering of the amino acid position as used herein refers to the method of "EU index" by Kabat et al (Kabat E A et al., 1991, Sequence of Proteins of Immunological Interest. 5th Ed. NIH, hereby incorporated by reference in its entirety).

The Fc region binds to an Fc receptor (FcR) present on the cell surface of effector cells, such as macrophages and NK cells. The Fc receptor participates in antibody-dependent cytotoxicity (ADCC), anaphylaxis reaction, id reaction, etc.

The type of Fc receptor varies, depending on the subtype of immunoglobulin. For example, Fc receptor of IgG is Fcγ receptor; Fc receptor of IgE is Fcε receptor; and Fc receptor of IgA is Fcα receptor.

The CH2-CH3 domain consists of the CH2 domain and the CH3 domain. The CH2-CH3 domain of a human IgG heavy chain is from the 233th alanine to the C-terminal.

Fc-Modified Antibody

The antibody of the invention is an Fc-modified antibody in which the amino acid sequence in the Fc region is modified. "Modification" or "site-specific mutagenesis (mutagenesis)" used in the invention includes substituting an original (unmodified) amino acid residue with any other amino acid residue, deletion of an original amino acid residue, and addition of an additional amino acid residue, but preferably indicates substitution of an original amino acid residue with any other amino acid residue. The original (unmodified) amino acid sequence as referred to herein is usually a natural Fc region sequence. In this context, "modification" and "mutagenesis" of amino acid residue are used in the same meaning.

In the invention, modification of amino acid residues may be effected by mutating the DNA that codes for the antibody.

In the invention, "mutation of DNA" means that DNA is mutated in such a manner that it may correspond to the amino acid residue to be modified. More specifically, it means that the DNA coding for the original amino acid residue is mutated to DNA coding for the amino acid residue to be modified. In general, it means genetic engineering or mutagenesis treatment for insertion, deletion or substitution of at least one nucleotide of the original DNA so as to give a codon that codes for the intended amino acid residue. Specifically, the codon that codes for the original amino acid residue is substituted with the codon that codes for the amino acid residue to be modified. Those skilled in the art may easily carry out such a DNA mutation according to a known technique, for example, according to a site-specific mutagenesis method such as PCR mutagenesis method (Hashimoto-Gogoh, T. et al., (1995) Gene 152, 271-275; Zoller, M J, and Smith, M., (1983) Methods Enzymol., 100, 468-500; Kramer, W. et al., (1984) Nucleic Acids, Res., 12, 9441-9456; Kramer W. and Fritz H J, (1987) Methods Enzymol., 154, 350-367; Kunkel, T A, (1985) Proc. Natl. Acad. Sci. USA, 82, 488-492; Kunkel, (1988) Methods Enzymol., 85, 2763-2766, all hereby incorporated by reference in its entirety).

The number of the amino acid residues in the Fc region to be modified in the invention is not specifically limited, but one or more (for example, from 1 to 30, or 2, 3, 4 or 5) amino acid residues may be modified.

Preferably, one or more of the amino acid residues at the positions 239, 298, 326, 330 and 332 in the Fc region are substituted with other amino acid residues. In addition, any amino acid residues of the Fc region may be substituted with those of any allotypes of IgG1, for example, with the amino acid residues of G1m(1) and nG1m(1).

The anti-glypican-3 antibody of the invention is not specifically limited so far as it binds to glypican-3, but preferably, the antibody specifically binds to glypican-3. The gene sequence and the amino acid sequence of glypican-3 are known (Lage, H. et al., Gene 188 (1997), 151-156, hereby incorporated by reference in its entirety). The anti-glypican-3 antibody of the invention is preferably IgG, more preferably IgG1.

Cytotoxicity

The anti-glypican-3 antibody of the invention containing modified Fc region exhibits enhanced cytotoxicity activity as compared with the anti-glypican-3 antibody having a natural or wild type Fc region.

Cytotoxicity activity includes, for example, antibody-dependent cell-mediated cytotoxicity (ADCC) activity, and complement-dependent cytotoxicity (CDC) activity. In the invention, the CDC activity means a cytotoxicity activity caused by a complement system; and the ADCC activity means that, when a specific antibody adheres to the cell surface antigen of a target cell, then an Fcγ receptor-having cell (e.g., immunocyte) binds to the Fc region via an Fcγ receptor to thereby impair the target cell.

Determination of whether an antibody has ADCC activity or CDC activity may be carried out according to a known method (for example, see Current Protocols in Immunology, Chapter 7, Immunologic Studies in Humans, Editor, John E. Coligan et al., John Wiley & Sons, Inc. (1993), hereby incorporated by reference in its entirety).

For example, the ADCC activity may be determined by mixing an effector cell, a target cell and an anti-glypican-3 antibody, then analyzing it for the degree of ADCC activity. The effector cell may include, for example, a mouse spleen cell, or a monocyte isolated from marrow or human peripheral blood. The target cell may include an established human cell line such as human hepatocyte cell line HuH-7. An anti-glypican-3 antibody is added to the target cell previously labeled with 51Cr and incubated, then an effector cell is added in a suitable ratio to the target cell. After incubation, the supernatant is collected and analyzed for radioactivity to determine the ADCC activity of the antibody.

The CDC activity may be determined by mixing the above-mentioned labeled target cell and an anti-glypican-3 antibody, adding a complement to the mixture and incubating, and then analyzing the supernatant for radioactivity.

Antibody

The term "antibody" as referred to herein is used in the broadest sense of the word, indicating any and every antibody that includes monoclonal antibody (including full-length monoclonal antibody), polyclonal antibody, antibody mutant, antibody fragment, poly-specific antibody (e.g., bispecific antibody), chimera antibody, humanized antibody and others, so far as it shows the desired biological activity.

Antibody and immunoglobulin are proteins having the same structure characteristics, and the antibody in the invention includes immunoglobulin.

The term "monoclonal antibody" as referred to herein indicates an antibody obtained from a group of substantially homogeneous antibodies, or that is, an antibody group in which all individual antibodies are uniform except minor mutants that may occur in nature. A monoclonal antibody is highly specific and generally acts on a single antigen site. Further, as compared with conventional polyclonal antibody preparations that typically include different antibodies to different epitopes, each monoclonal antibody is directed to a single epitope on an antigen. In addition to the specificity thereof, a monoclonal antibody has another advantage in that it is synthesized through culture of a hybridoma which is not contaminated with any other antibodies. The modifier "monoclonal" suggests the nature of the antibody obtained from a group of substantially uniform antibodies, and it does not require that the antibody be produced by a specific method. For example, the monoclonal antibody for use in the invention may be produced, for example, according to a hybridoma method (Kohler and Milstein, Nature 256:495 (1975), hereby incorporated by reference in its entirety), or a recombination method (U.S. Pat. No. 4,816,567, hereby incorporated by reference in its entirety). The monoclonal antibody for use in the invention may also be isolated from a phage antibody library (Clackson et al., Nature 352:624-628 (1991); Marks et al., J. Mol. Biol., 222:581-597 (1991), all hereby incorporated by reference in its entirety).

The term "antibody fragment" indicates a portion of a full-length antibody. The antibody fragment for use in the invention is preferably an antibody fragment that maintains an antibody-binding activity and maintains a cytotoxicity activity of the full-length antibody.

A multi-specific antibody is an antibody having specificity to at least two different antigens. In general, this type of molecule may bind to two antigens (that is, bispecific antibody), but in this description, the "multi-specific antibody" includes antibodies having specificity to more than two (for example, three) antigens. The multi-specific antibody may be a full-length antibody or a fragment of such an antibody. For example, the bispecific antibody may recognize two different antigens or may recognize different epitopes of one antigen. In addition, one may recognize a cytotoxic substance.

The antibody of the present invention may also be a chimera antibody or a humanized antibody. In general, a chimera antibody comprises a variable region derived from an antibody of a non-human mammal, and a constant region derived from a human antibody. On the other hand, humanized antibody comprises a complementarity-determining region derived from a non-human mammal, and a framework region and a constant region derived from a human antibody.

The origin of the variable region in a chimera antibody, and the origin of a CDR in a humanized antibody are not specifically limited, but may be derived from any animals. For example, any sequences derived from mouse antibody, rat antibody, rabbit antibody, or camel antibody may be used (Cook W J et al., Protein Eng. 1996 July 9(7):623-8; Tsurushita N et al., J Immunol Methods. 2004 December 295(1-2):9-19; Sato K et al, Mol. Immunol. 1994 April 31(5):371-81; Preparation of genetically engineered monoclonal antibodies for human immunotherapy. Hum Antibodies Hybridomas. 1992 July 3(3):137-45; Genetically engineered antibodies: progress and prospects. Crit. Rev Immunol. 1992; 12(3-4):125-68, all hereby incorporated by reference in its entirety).

For the constant region of a chimera antibody and a humanized antibody, those derived from a human antibody may be used. For example, Cγ1, Cγ2, Cγ3, Cγ4 may be used for the H-chain, and Cκ and Cλ may be used for the L-chain.

Chimera antibody is an antibody constructed by combining sequences derived from different animals, and for example, it is an antibody comprising the heavy chain and light chain variable regions of a mouse antibody and the heavy chain and light chain constant regions of a human antibody. Such a chimera antibody may be constructed in any known methods. For example, a DNA coding for a mouse antibody variable region and a DNA coding for a human antibody constant region are ligated, then inserted into an expression vector, and introduced into a host to produce the intended antibody.

A humanized antibody, also referred to as a reshaped human antibody, is constructed by transplanting a complementarity-determining region (CDR) of an antibody of a mammal except human, for example, a mouse antibody into the complementarity-determining region of a human antibody. A general genetic recombination method for making a humanized antibody is known in the art (see EP 125023; WO96/02576, hereby incorporated by reference in its entirety).

Specifically, a DNA sequence designed so as to ligate CDR of a mouse antibody with the framework region (FR) of a human antibody may be synthesized through PCR using, as a primer, several oligonucleotides constructed so as to have portions overlapping with the terminal region of both CDR and FR (see the method described in WO98/13388, hereby incorporated by reference in its entirety).

The framework region of a human antibody to be ligated with CDR is so selected that the complementarity-determining region may form a good antigen-binding site. If desired, the amino acids in the framework region of the variable region of the antibody may be substituted in order that the complementarity-determining region of the reshaped human antibody may form a suitable antigen-binding site (Sato, K. et al., Cancer Res. (1993) 53, 851-856, hereby incorporated by reference in its entirety).

In addition, those antibodies are also included in the antibody of the invention which have mutation in one or more amino acids in regions other than the specified sites in the Fc region mentioned above or CDR region, and which is functionally equivalent to the antibody of the invention.

For preparing a polypeptide that comprises a different amino acid sequence but is functionally equivalent to a certain polypeptide, a method of introducing a mutation into the polypeptide is well known to those skilled in the art. For example, those skilled in the art may introduce a mutation to the antibody of the invention according to a site-specific mutagenesis or the like to thereby prepare an antibody functionally equivalent to that antibody. Amino acid mutation may also occur spontaneously.

Preferably, an amino acid residue is mutated to another amino acid residue which has side chain properties close to that of the original one. For example, regarding the properties thereof, amino acid side chains include hydrophobic amino acids (A, I, L, M, F, P, W, Y, V), hydrophilic amino acids (R, D, N, C, E, Q, G, H, K, S, T), aliphatic side chain-having amino acids (G, A, V, L, I, P), hydroxyl group-containing side chain-having amino acids (S, T, Y), sulfur atom-containing side chain-having amino acids (C, M), carboxylic acid and amido-containing side chain-having amino acids (D, N, E, Q), base-containing side chain-having amino acids (R, K, H), aromatic side chain-having amino acids (H, F, Y, W) (the parenthesized alphabets are the one-letter code for amino acids). It is known that a polypeptide having an amino acid sequence modified from the original amino acid sequence through deletion, addition and/or substitution with any other amino acid of one or more amino acid residues therein still substantially maintain the biological activity of the original polypeptide (Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G., et al., Proc. Natl. Acad. Sci. USA (1982) 79, 6409-6413, all hereby incorporated by reference in its entirety).

The antibody for use in the invention may be a conjugated antibody bound with a various types of molecules, such as non-peptidic polymers such as polyethylene glycol (PEG), radioactive substances and toxins. Such a conjugated antibody may be obtained through chemical modification of the antibody. The method of chemical modification has been established in the art. The antibody of the invention may include these conjugated antibodies (D. J. King., Applications and Engineering of Monoclonal antibodies., 1998 T. J. International Ltd, Monoclonal Antibody-Based Therapy of Cancer., 1998 Marcel Dekker Inc; Chari et al., Cancer Res., 1992 Vol 152:127; Liu et al., Proc Natl Acad Sci USA., 1996 Vol 93:8681, all hereby incorporated by reference in its entirety).

Antibody Preparation

The antibody of the invention may be produced according to a method known to those skilled in the art. Specifically, DNA coding for the intended antibody is inserted into an expression vector. In this step, DNA is inserted into an expression vector in such a manner that it could be expressed under control of an expression control region, for example, an enhancer and a promoter. Next, a host cell is transformed with the expression vector and the antibody is expressed in the host cell. In this process, a combination of a suitable host and a suitable expression vector may be used.

Examples of the vector include M13 vector, pUC vector, pBR322, pBluescript, pCR-Script. For subcloning and separation of cDNA, for example, pGEM-T, pDIRECT and pT7 may also be used.

Expression vectors are especially useful for the purpose of antibody production. When *E. coli* such as JM109, DH5α, HB101 or XL1-Blue is used as a host, the expression vector must indispensably have a promoter that drives efficient expression of the vector in *E. coli*, for example, lacZ promoter (Ward et al., Nature (1989) 341, 544-546; FASEB J. (1992) 6, 2422-2427, hereby incorporated by reference in its entirety), araB promoter (Better et al., Science (1988) 240, 1041-1043, hereby incorporated by reference in its entirety) or T7 promoter. The vector of this type also includes pGEX-5X-1 (Pharmacia), QIA express system (QIAGEN), pEGFP, and pET (in this case, the host is preferably a T7 RNA polymerase-expressing BL21).

The vector may include a signal sequence for polypeptide secretion. For the signal sequence for polypeptide secretion, for example, pelB signal sequence (Lei, S. P. et al., Bacteriol. (1987) 169, 4397, hereby incorporated by reference in its entirety) may be used for production in periplasm of *E. coli*. The introduction of the vector into a host cell may be effected, for example, according to a calcium chloride method or an electroporation method.

In addition to the *E. coli* expression vectors, the vector used for polypeptide production in the invention includes, for example, mammal-derived expression vectors (e.g., pcDNA3 (Invitrogen), pEGF-BOS (Nucleic acids, Res., 1990, 18(17), p. 5322, hereby incorporated by reference in its entirety), pEF, pCDM8); insect cell-derived expression vectors (e.g., Bac-toBAC baculovairus expression system (GIBCO BRL), pBacPAK8); vegetable-derived expression vectors (e.g., pMH1, pMH2); animal virus-derived expression vectors (e.g., pHSV, pMV, pAdexLcw), retrovirus-derived expression vectors (e.g., pZIPneo), yeast-derived expression vectors (e.g., *Pichia* Expression Kit (Invitrogen), pNV11, SP-Q01), *Bacillus subtilis*-derived expression vectors (e.g., pPL608, pKTH50).

For expression in animal cells such as CHO cells, COS cells or NIH3T3 cells, the vector must indispensably have a promoter necessary for intracellular expression, for example, SV40 promoter (Mulligan et al., Nature (1979) 277, 108, hereby incorporated by reference in its entirety), MMTV-LTR promoter, EF1α promoter (Mizushima et al., Nucleic Acids Res. (1990) 18, 5322, hereby incorporated by reference in its entirety), CAG promoter (Gene (1991) 108, 193, hereby incorporated by reference in its entirety), CMV promoter. Preferably, the vector has a gene for screening of the transformed cells (e.g., drug-resistant gene capable of being differentiated by drug (e.g., neomycin, G418)). The vector having such characteristics includes, for example, pMAM, pDR2, pBK-RSV, pBK-CMV, pOPRSV, pOP13.

Further, for the purpose of stable gene expression and an increase in the number of gene copies in cells, a vector having a complementary DHFR gene (e.g., pCHOI) is introduced into CHO cells deficient in the nucleic acid synthetic pathway to complement the deficiency and is amplifyed with methotrexate (MTX). For the purpose of transient expression of the gene, COS cells having an SV40T antigen-expressing gene on the chromosome is transformed with a vector having SV40 replication origin (e.g., pcD). The replication origin may also be derived from polyoma virus, adeno virus, bovine polyoma virus (BPV), etc. Further, for increasing the number of gene copies in a host cell system, the expression vector may contain a selected marker, such as aminoglycoside transferase (APH) gene, thymidine kinase (TK) gene, *E. coli* xanthine-guanine phosphoribosyl transferase (Ecogpt) gene, dihydrofolate reductase (dhfr) gene.

Pharmaceutical Composition

The invention also relates to a pharmaceutical composition containing the antibody of the invention. Since the antibody of the invention exhibits enhanced cytotoxicity activity, it is suitable for use in pharmaceutical compositions, and in particular, it is useful as an anticancer agent. Since it has been shown that an anti-glypican-3 antibody has a cytotoxicity against a hepatoma-derived cell line (e.g. WO03/00883, hereby incorporated by reference in its entirety), the antibody of the invention is particularly useful as a drug for treating hepatic cancer. When the antibody of the invention is used in pharmaceutical compositions, it is preferably a humanized antibody in view of the antigenicity to humans.

The pharmaceutical composition of the invention may contain a pharmaceutically-acceptable carrier. The pharmaceutically-acceptable carrier includes, for example, sterile water, physiological saline, stabilizer, excipient, antioxidant (e.g., ascorbic acid), buffer (e.g., phosphoric acid, citric acid, other organic acids), preservative, surfactant (e.g., PEG, Tween), chelating agent (e.g., EDTA), or binder. In addition, the pharmaceutical composition of the invention may further contain any other low-molecular polypeptides; proteins such as serum albumin, gelatin, or immunoglobulin; amino acids such as glycine, glutamine, asparagine, arginine, lysine; saccharides such as polysaccharides, monosaccharides; carbohydrates; sugar alcohols such as mannitol, sorbitol. When the composition is prepared as an aqueous solution for injection, it may be combined with an isotonic solution containing, for example, physiological saline, glucose or any other auxiliary agent, such as D-sorbitol, D-mannose, D-mannitol, sodium chloride, and with a suitable dissolution aid such as alcohol (e.g., ethanol), polyalcohol (e.g., propylene glycol, PEG), nonionic surfactant (e.g., Polysorbate 80, HCO-50).

If desired, the composition may be encapsulated into microcapsules (microcapsules of hydroxymethyl cellulose, gelatin, poly(methyl methacrylate), etc.), or may be formed into colloid drug delivery systems (e.g., liposomes, albumin microspheres, microemulsions, nanoparticles, nanocapsules) (see Remington's Pharmaceutical Science, 16th edition, Oslo Ed., 1980, hereby incorporated by reference in its entirety). Further, a method of formulating slow-release drugs is known and may be applicable to the invention (Langer et al., J. Biomed. Mater. Res., 1981, 15:167-277; Langer, Chem. Tech., 1982, 12:98-105; U.S. Pat. No. 3,773, 919; EP 58,481; Sidman et al., Biopolymers 1983, 22:547-556; EP 133,988).

The composition may be administered to patients either orally or parenterally, but preferably parenterally. The shape (preparation form) of the pharmaceutical composition of the invention is not specifically limited but includes, for example, injections, transnasal preparations, transpulmonary preparations, percutaneous preparations, freeze-dried preparations, solutions. Preferred are freeze-dried preparations.

Freeze-drying may be effected in any method well known to those skilled in the art (Pharm. Biotechnol., 2002, 13, 109-133; Int. J. Pharm., 2000, 203(1-2), 1-60; Pharm. Res., 1997, 14(8), 969-975, all hereby incorporated by reference in its entirety). For example, a solution of the composition is suitably aliquoted into freeze-drying vials or the like vessels, and put in a freezer or a freeze-dryer, or dipped in a coolant such as acetone/dry ice and liquid nitrogen. When the antibody preparation is formed into a high-concentration solution preparation, it may be prepared according to a method well known to those skilled in the art. For example, a membrane concentration method using a TFF membrane may be employed as described in J. Pharm. Sci., 2004, 93(6), 1390-1402, hereby incorporated by reference in its entirety.

The formulation for injection may be systemically or topically administered in a mode of, for example, intravenous injection, intramuscular injection, intraperitoneal injection or subcutaneous injection. Depending on the age and the condition of the patient to which the composition is administered, the administration method for it may be suitably selected. The dose may be selected, for example, from a range of from 0.0001 mg/kg of body weight to 1000 mg/kg of body weight for a unit dose. Alternatively, the dose may be selected from a range of from 0.001 to 100000 mg/body. However, the invention should not be limited to the dose and the administration method as above.

The invention is described in more detail with reference to the following Examples, to which, however, the invention should not be limited.

EXAMPLES

Example 1: Production of Fc-Modified Anti-GPC3 Antibody

Example 1-1: Preparation of Fc Cassettes for Mutagenesis

Fc-modified humanized anti-GPC3 antibodies having amino acid substitutions shown in the table below in the amino acid sequence of the H-chain shown in SEQ ID NO: 19. FIG. 1 shows the structure and preparation strategy of the Fc-modified antibodies of the invention.

| | |
|---|---|
| V22 | I332E |
| V209 | S239D/A330L/I332E |
| V212 | S239D/S298A/I332E |
| V922 | S239D/K326T/I332E |
| V1608 | S239D/S298A/K326T/I332E |
| V209nG1m (1) | S239D/A330L/I332E/D356E/L358M |

Using primers shown by SEQ ID NO:1 to NO:9, Fc-mutation cassettes for constructing five types of Fc-modified antibodies named V22, V209, V212, V922 and V1608 were produced according to a PCR-Walking method. Specifically, primers commonF1 and commonR1 were used for V22, V209 and V922; and primers 212-F1 and 212-F1 were used for V212 and V1608. A first-stage PCR was carried out in a PCR reaction solution mentioned below:

×10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), dH$_2$O 35.5 µl, and 5 units/µl KOD polymerase 0.5 µl were added to make 50 µl in total. PCR was carried out under the condition mentioned below.

96° C. 1 min; (98° C. 15 sec; 65° C. 2 sec; 74° C. 15 sec)×2 cycles; 74° C. 30 sec; 4° C.

One microliter of the first stage-amplified product was taken out and used in the next, second-stage PCR reaction. Specifically, primers CommonF2 and 212-R2 were used for V22 and V212; primers CommonF2 and 209-R2 were used for V209; primers CommonF2 and 922-R2 were used for V922; and primers CommonF2 and 1608-R2 were used for V1608. The second-stage PCR was carried out in a PCR reaction solution mentioned below:

×10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), 1 µl of the first stage-amplified product as a template, dH$_2$O 35.5 µl, and 5 units/µl KOD polymerase 0.5 µl were added to make 51 µl in total. PCR was carried out under the condition mentioned below.

96° C. 1 min; (98° C. 15 sec; 65° C. 2 sec; 74° C. 15 sec)×5 cycles; 74° C. 30 sec; 4° C.

One microliter of the second stage-amplified product was taken out and used in the next, third-stage PCR reaction. Specifically, primers CommonF3 and CommonR3 were used for V22, V209, V212, V922 and V1608, and the third-stage PCR was carried out in a PCR reaction solution mentioned below.

×10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), 1 µl of the second stage-amplified product as a template, dH$_2$O 35.5 µl, and 5 units/µl KOD polymerase 0.5 µl were added to it to make 51 µl in total. Using this, PCR was carried out under the condition mentioned below.

96° C. 1 min; (98° C. 15 sec; 65° C. 2 sec; 74° C. 20 sec)×35 cycles; 74° C. 1 min; 4° C.

Each fragment obtained was subcloned into pBluescriptSK$^+$ and its sequence was confirmed.

```
Forward primer: 212-F1
                                        (SEQ ID NO: 1)
agttcaactggtacgtggacggcgtggaggtgcataatgccaagaca
aagccgcgggaggagcagtacaacgccacgtaccgtgtggtcagcgt
cc Forward primer: commonF2
                                        (SEQ ID NO: 2)
tctcccggacccctgaggtcacatgcgtggtggtggacgtgagccac
gaagaccctgaggtcaagttcaactggtacgtggacggcgtggagg Forward primer: commonF3
                                        (SEQ ID NO: 3)
gcacctgagctcctgggggaccggacgtatcctcttcccccccaaaa
cccaaggacaccctcatgatctcccggacccctgaggtcacatgcgt
gg Reverse primer: 212-R1
                                        (SEQ ID NO: 4)
ggagaccttgcacttgtactccttgccattcagccagtcctggtgca
ggacggtgaggacgctgaccacacggtacgtggcgttgtactgctcc
```

-continued

```
Reverse primer: 209-R2
                                                (SEQ ID NO: 5)
ggctgcccttggctttggagatggttttctcctcgggcagtgggag
ggctttgttggagaccttgcacttgtactccttgccattcagcc Reverse primer: 212-R2
                                                (SEQ ID NO: 6)
ggctgcccttggctttggagatggttttctcctcggggctgggag
ggctttgttggagaccttgcacttgtactccttgccattcagcc Reverse primer: 922-R2
                                                (SEQ ID NO: 7)
ggctgcccttggctttggagatggttttctcctcggggctgggag
ggcggtgttggagaccttgcacttgtactccttgccattcagcc Reverse primer: 1608-R2
                                                (SEQ ID NO: 8)
ggctgcccttggctttggagatggttttctcctcggggctgggag
ggcctcgttggagaccttgcacttgtactccttgccattcagcc Reverse primer: commonR3
                                                (SEQ ID NO: 9)
gagctccccgggatggggcagggtgtacacctgtggttctcgggc
tgcccttttggctttggagatggttttctcctcgg
```

Example 1-2: Preparation of Vector Expressing Fc-Modified Anti-GPC3 Antibody A vector for expressing the Fc-modified anti-GPC3 antibody of the invention was constructed based on a gene coding for a humanized anti-glypican-3 antibody previously prepared by the inventors (H-chain, SEQ ID NO: 10; L-chain, SEQ ID NO: 11), which is referred to as "wild-type" in the following Examples.

The amino acid sequences of the H-chain variable region and L-chain variable region of the wild-type humanized anti-GPC3 antibody are shown in SEQ ID NO: 21 (ver.k) and SEQ ID NO: 22 (ver.a), respectively. The CDR sequences of the wild-type humanized anti-GPC3 antibody are shown below.

```
H-chain
CDR1
                                               (SEQ ID NO: 23)
DYEMH CDR2
                                               (SEQ ID NO: 24)
ALDPKTGDTAYSQKFKG

CDR3
                                               (SEQ ID NO: 25)
FYSYTY

L-chain
CDR1
                                               (SEQ ID NO: 26)
RSSQSLVHSNGNTYLH

CDR2
                                               (SEQ ID NO: 27)
KVSNRFS

CDR3
                                               (SEQ ID NO: 28)
SQNTHVPPT
```

Using the anti-human GPC3 antibody H-chain gene shown by SEQ ID NO:10 as a template, and using a primer of SEQ ID NO:11 and a primer of SEQ ID NO:12 with a SacI site previously introduced as silent mutation, PCR was carried out under the condition mentioned below.

×10 KOD buffer 5 μl, dNTPs and MgCl$_2$ 5 μl and 2 μl, respectively, (attached to KOD polymerase, Toyobo) were mixed. The primer combination as above (20 μmole/l, 1 μl each), 1 μl of GPC3 antibody H-chain gene as a template, dH$_2$O 34.5 μl, and 5 units/μl KOD polymerase 0.5 μl were added to make 50 μl in total. PCR was carried out under the condition mentioned below.

96° C. 1 min; (98° C. 15 sec; 65° C. 2 sec; 74° C. 30 sec)×35 cycles; 74° C. 30 sec; 4° C.

The fragment obtained was introduced into the SmaI site of pBluescriptSK$^+$ (pB-Sacless), in which the SacI site had been previously filled up with a DNA blunting kit (Takara Bio), and its sequence was confirmed (pB-GPCSacmt). Next, from a vector containing an anti-GPC3 antibody H-chain gene shown by SEQ ID NO:10, an SmaI-BamHI fragment of about 290 bp, corresponding to the C-terminal sequence of anti-human GPC3 antibody H-chain, was cut out, and introduced into the corresponding site of pB-GPCSacmt (pB-GPCSacmtC). Next, the Fc-mutation cassette of V22, V209, V212, V922 or V1608 produced in Example 1-1 was introduced into the SacI-SmaI site of pB-GPCSacmtC, and the sequence of pB-GPCSacmtC was confirmed. Further, for completing construction of the mutated H-chain, an EcoRI-NheI fragment of about 415 bp of the GPC3 antibody H-chain gene shown by SEQ ID NO:10 was ligated with it to obtain a gene coding for Fc-mutated H-chain.

The resultant gene coding for a mutated H-chain was cleaved with EcoRI-NotI, and introduced into the corresponding site of an animal cell expression vector pCXND3 (pC-aGPCh). Next, a fragment of about 3.1 kb, containing an anti-GPC3 antibody L-chain gene shown by SEQ ID NO:13 and a promoter region, was cleaved with HindIII, and ligated with the corresponding site of pC-aGPCh to obtain an anti-GPC3 antibody expression vector (pC-aGPChl). The vector pC-aGPChl to V22, V209, V212, V922 and V1608 was designated as pC-aGPChl(22), pC-aGPChl(209), pC-aGPChl(212), pC-aGPChl(922) and pC-aGPChl(1608), respectively.

The amino acid sequence of the H chain of V22, V209, V212, V922 and V1608 are shown in V22 (SEQ ID NO: 29), V209 (SEQ ID NO: 30), V212 (SEQ ID NO: 31), V922 (SEQ ID NO: 32) and V1608 (SEQ ID NO: 33), respectively. The amino acid sequence of the CH2-CH3 domain of V22, V209, V212, V922 and V1608 are shown in V22 CH2-CH3 domain (SEQ ID NO: 34), V209 CH2-CH3 domain (SEQ ID NO: 35), V212 CH2-CH3 domain (SEQ ID NO: 36), V922 CH2-CH3 domain (SEQ ID NO: 37) and V1608 CH2-CH3 domain (SEQ ID NO: 38), respectively.

```
anti-human GPC3 antibody H-chain
                                               (SEQ ID NO: 10)
GAATTCCACCATGGACTGGACCTGGAGGTTCCTCTTTGTGGTGGCAGCA

GCTACAGGTGTCCAGTCCCAGGTGCAGCTGGTGCAGTCTGGAGCTGAGG

TGAAGAAGCCTGGGGCCTCAGTGAAGGTCTCCTGCAAGGCTTCTGGATA

CACCTTCACCGACTATGAAATGCACTGGGTGCGACAGGCCCCTGGACAA

GGGCTTGAGTGGATGGGAGCTCTTGATCCTAAAACTGGTGATACTGCCT

ACAGTCAGAAGTTCAAGGGCAGAGTCACGCTGACCGCGGACAAATCCAC

GAGCACAGCCTACATGGAGCTGAGCAGCCTGACATCTGAGGACACGGCC

GTGTATTACTGTGTACAAGATTCTACTCCTATACTTACTGGGGCCAGGGAA

CCCTGGTCACCGTCTCCTCAGCTAGCACCAAGGGCCCATCGGTCTTCCC

CCTGGCACCCTCCTCCAAGAGCACCTCTGGGGGCACAGCGGCCCTGGGC
```

-continued

TGCCTGGTCAAGGACTACTTCCCCGAACCGGTGACGGTGTCGTGGAACT

CAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGC

TTGGGCACCCAGACCTACATCTGCAACGTGAATCACAAGCCCAGCAACA

CCAAGGTGGACAAGAAAGTTGAGCCCAAATCTTGTGACAAAACTCACAC

ATGCCCACCGTGCCCAGCACCTGAACTCCTGGGGGGACCGTCAGTCTTC

CTCTTCCCCCCAAAACCCAAGGACACCCTCATGATCTCCCGGACCCCTG

AGGTCACATGCGTGGTGGTGGACGTGAGCCACGAAGACCCTGAGGTCAA

GTTCAACTGGTACGTGGACGGCGTGGAGGTGCATAATGCCAAGACAAAG

CCGCGGGAGGAGCAGTACAACAGCACGTACCGTGTGGTCAGCGTCCTCA

CCGTCCTGCACCAGGACTGGCTGAATGGCAAGGAGTACAAGTGCAAGGT

CTCCAACAAAGCCCTCCCAGCCCCCATCGAGAAAACCATCTCCAAAGCC

AAAGGGCAGCCCCGAGAACCACAGGTGTACACCCTGCCCCCATCCCGGG

ATGAGCTGACCAAGAACCAGGTCAGCCTGACCTGCCTGGTCAAAGGCTT

CTATCCCAGCGACATCGCCGTGGAGTGGGAGAGCAATGGGCAGCCGGAG

AACAACTACAAGACCACGCCTCCCGTGCTGGACTCCGACGGCTCCTTCT

TCCTCTACAGCAAGCTCACCGTGGACAAGAGCAGGTGGCAGCAGGGGAA

CGTCTTCTCATGCTCCGTGATGCATGAGGCTCTGCACAACCACTACACG

CAGAAGAGCCTCTCCCTGTCTCCGGGTAAATGATAAGCGGCCGCGGATCC

Forward primer: NS-F
(SEQ ID NO: 11)
gctagcaccaagggcccatcggtcttccccctggcaccctcctcc Reverse primer: NS-R
(SEQ ID NO: 12)
gagctcaggtgctgggcacggtgggcatgtgtgagttttgtcac anti-human GPC3 antibody L-chain
(SEQ ID NO: 13)
AAGCTTGCATGCCTGCAGGTCGACTCTAGAGGATCCGTCGACATTGATTA

TTGACTAGTTATTAATAGTAATCAATTACGGGGTCATTAGTTCATAGCCC

ATATATGGAGTTCCGCGTTACATAACTTACGGTAAATGGCCCGCCTGGCT

GACCGCCCAACGACCCCCGCCCATTGACGTCAATAATGACGTATGTTCCC

ATAGTAACGCCAATAGGGACTTTCCATTGACGTCAATGGGTGGAGTATTT

ACGGTAAACTGCCCACTTGGCAGTACATCAAGTGTATCATATGCCAAGTA

CGCCCCCTATTGACGTCAATGACGGTAAATGGCCCGCCTGGCATTATGCC

CAGTACATGACCTTATGGGACTTTCCTACTTGGCAGTACATCTACGTATT

AGTCATCGCTATTACCATGGTCGAGGTGAGCCCCACGTTCTGCTTCACTC

TCCCCATCTCCCCCCCCTCCCCACCCCCAATTTTGTATTTATTTATTTTT

TAATTATTTTGTGCAGCGATGGGGGCGGGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGCGCTGCCTTCGCCCCGTGCCCCGCTCCGCCGCCGCCTCGC

GCCGCCCGCCCCGGCTCTGACTGACCGCGTTACTCCCACAGGTGAGCGGG

-continued

CGGGACGGCCCTTCTCCTCCGGGCTGTAATTAGCGCTTGGTTTAATGACG

GCTTGTTTCTTTTCTGTGGCTGCGTGAAAGCCTTGAGGGGCTCCGGGAGG

GCCCTTTGTGCGGGGGGAGCGGCTCGGGGGGTGCGTGCGTGTGTGTGTGC

GTGGGGAGCGCCGCGTGCGGCTCCGCGCTGCCCGGCGGCTGTGAGCGCTG

CGGGGCGCGGCGCGGGGCTTTGTGCGCTCCGCAGTGTGCGCGAGGGGAGCG

CGGCCGGGGGCGGTGCCCCGCGGTGCGGGGGGGCTGCGAGGGGAACAAA

GGCTGCGTGCGGGGTGTGTGCGTGGGGGGTGAGCAGGGGGTGTGGGCGC

GTCGGTCGGGCTGCAACCCCCCTGCACCCCCCTCCCCGAGTTGCTGAGC

ACGGCCCGGCTTCGGGTGCGGGGCTCCGTACGGGGCGTGGCGCGGGGCTC

GCCGTGCCGGGCGGGGGTGGCGGCAGGTGGGGGTGCCGGGCGGGGCGGG

GCCGCCTCGGGCCGGGAGGGCTCGGGGAGGGGCGCGGCGGCCCCCGGA

CGCGCGGCGGCTGTCGAGGCGCGGCGAGCCGCAGCCATTGCCTTTTATGG

TAATCGTGCGAGAGGGCGCAGGGACTTCCTTTGTCCCAAATCTGTGCGGA

GCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCG

TCGCCGCGCCGCCGTCCCCTTCTCCCTCTCCAGCCTCGGGGCTGTCCGCG

GGGGGACGGCTGCCTTCGGGGGGGACGGGGCAGGGCGGGGTTCGGCTTCT

GGCGTGTGACCGGCGGCTCTAGAGCCTCTGCTAACCATGTTCATGCCTTC

TTCTTTTTCCTACAGCTCCTGGGCAACGTGCTGGTTATTGTGCTGTCTCA

TCATTTTGGCAAAGAATTCCTCGAGCCACCATGAGGCTCCCTGCTCAGCT

CCTGGGGCTGCTAATGCTCTGGGTCTCTGGATCCAGTGGGGATGTTGTGA

TGACTCAGTCTCCACTCTCCCTGCCCGTCACCCCTGGAGAGCCGGCCTCC

ATCTCCTGCAGATCTAGTCAGAGCCTTGTACACAGTAATAGGAACACCTA

TTTACATTGGTACCTGCAGAAGCCAGGGCAGTCTCCACAGCTCCTGATCT

ATAAAGTTTCCAACCGATTTTCTGGGGTCCCTGACAGGTTCAGTGGCAGT

GGATCAGGCACAGATTTTACACTGAAAATCAGCAGAGTGGAGGCTGAGGA

TGTTGGGGTTTATTACTGCTCTCAAAATACACATGTTCCTCCTACGTTTG

GCCAGGGGACCAAGCTGGAGATCAAACGTACGGTGGCTGCACCATCTGTC

TTCATCTTCCCGCCATCTGATGAGCAGTTGAAATCTGGAACTGCCTCTGT

TGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAG

CAGGACAGCAAGGACAGCACCTACAGCCTCAGCAGCACCCTGACGCTGAG

CAAAGCAGACTACGAGAAACACAAAGTCTACGCCTGCGAAGTCACCCATC

AGGGCCTGAGCTCGCCCGTCACAAAGAGCTTCAACAGGGGAGAGTGTTGA

TAAGTCGAGGTCGAGGAATTCACTCCTCAGGTGCAGGCTGCCTATCAGAA

GGTGGTGGCTGGTGTGGCCAATGCCCTGGCTCACAAATACCACTGAGATC

TTTTTCCCTCTGCCAAAAATTATGGGGACATCATGAAGCCCCTTGAGCAT

CTGACTTCTGGCTAATAAAGGAAATTTATTTTCATTGCAATAGTGTGTTG

GAATTTTTTGTGTCTCTCACTCGGAAGGACATATGGGAGGGCAAATCATT

TAAAACATCAGAATGAGTATTTGGTTTAGAGTTTGGCAACATATGCCCAT

ATGCTGGCTGCCATGAACAAAGGTTGGCTATAAAGAGGTCATCAGTATAT

-continued

```
GAAACAGCCCCCTGCTGTCCATTCCTTATTCCATAGAAAAGCCTTGACTT

GAGGTTAGATTTTTTTTATATTTTGTTTTGTGTTATTTTTTTCTTTAACA

TCCCTAAAATTTTCCTTACATGTTTTACTAGCCAGATTTTTCCTCCTCTC

CTGACTACTCCCAGTCATAGCTGTCCCTCTTCTCTTATGGAGATCCCTCG
ACCTGCAGCCCAAGCTT
```

Example 1-3: Production of V209 nGlm(1) Allotype

For obtaining an nGlm(1) allotype of V209, a Glm(1) allotype thereof, a cassette for nGlm(1) allotype was formed. Specifically, using forward primer HerSmaF and reverse primer HerNotR shown by SEQ ID NO: 14 and NO:15, and using, as a template, the anti-GPC3 antibody H-chain gene shown by SEQ ID NO:10 and produced in Example 1-2, PCR was carried out under the condition mentioned below.

×10 KOD buffer 5 µl, dNTPs and MgCl$_2$ 5 µl and 2 µl, respectively, (attached to KOD polymerase, Toyobo) were mixed. The primer combination as above (20 mmole/l, 1 µl each), GPC3 antibody H-chain gene 1 µl, dH$_2$O 34.5 µl, and 5 units/µl KOD polymerase 0.5 µl were added to make 50 µl in total. PCR was carried out under the condition mentioned below.

96° C. 1 min; (98° C. 15 sec; 65° C. 2 sec; 74° C. 30 sec)×35 cycles; 74° C. 30 sec; 4° C.

The fragment obtained was subcloned into pBluescriptSK$^+$ (pBher), and its sequence was confirmed. Next, an SmaI-NotI fragment of about 290 bp was cut out from pC-aGPChl(209) described in Example 1-2. On the other hand, SmaI-NotI fragment was cut out from pBher in the same manner, and the fragment of about 290 bp was introduced into the corresponding site of pC-aGPChl(209) for substitution to obtain a nGlm(1) allotype expression vector (pC-aGPChl(209Her)).

```
Forward primer:
HerSmaF
                                        (SEQ ID NO: 14)
gggaggagatgaccaagaaccaggtcaccctgacctgcc Reverse primer:
HerNotR
                                        (SEQ ID NO: 15)
tttgcggccgcttatcatttacccggagacagggagaggctc
```

Example 2: Preparation of Fc-Modified Anti-GPC3 Antibody

Example 2-1: Expression of Fc-Modified Anti-GPC3 Antibody in CHO Cells

Ten microliters of Fc-modified anti-GPC3 antibody expression vector pC-aGPChl(22), pC-aGPChl(209), pC-aGPChl(212), pC-aGPChl(922), pC-aGPChl(1608) or pC-aGPChl(209Her) was cleaved with PvuI to give a linear DNA. This was introduced into 2×10$^6$/0.6 ml PBS(−) of CHO cells (strain DXB11S) according to an electroporation method under a condition of 1.5 kV and 25 uF. The cells were incubated in a 8% CO$_2$ incubator at 37° C. The cells were screened in CHO-S-SFMII medium (Invitrogen) containing 400 µg/ml of geneticin. Selected cells were inoculated into a CHO-S-SFMII medium containing 400 µg/ml geneticin in a 96-well plate at 0.4 cells/100 µl/well, and the cells were cloned according to a limiting dilution method. The culture supernatant was analyzed with BIACORE 3000. The antigen was quantified using a chip with fused protein GST-GPC3 (antigen GST and human glypican-3 shown by SEQ ID NO:16) immobilized thereon, and high-expression cells were selected.

```
Amino acid sequence of GPC3 peptide
                                        (SEQ ID NO: 16)
AELAYDLDVDDAPGNSQQATPKDNEISTFHNLGNVHSPLK
```

Example 2-2: Purification of Fc-Modified Anti-GPC3 Antibody

The culture supernatant of CHO cells expressing Fc-modified humanized glypican antibody was applied to an rProtein A Sepharose Fast Flow column equilibrated with 150 mM NaCl-containing 10 mM citrate-phosphate buffer (pH 7.5). The column was washed with the same buffer, 1 M NaCl-containing 10 mM citrate-phosphate buffer (pH 7.5), then 10 mM citrate-phosphate buffer (pH 7.5), and the protein adsorbed to the column was eluted out with 20 mM acetic acid. To the 20 mM acetic acid fraction containing Fc-modified humanized anti-glypican antibody, 1 M tris-HCl buffer (pH 8.5) was added to adjust pH of from 5 to 6, and was filtered through a 0.22 µm filter. An equivalent amount of MilliQ water was added to the thus-filtered fraction, and applied to SP Sepharose Fast Flow column equilibrated with 20 mM acetate buffer (pH 6.0). The column was washed with the same buffer, and then the protein adsorbed to the column was eluted out with 20 mM NaCl-containing 20 mM acetate buffer (pH 6.0) to obtain a purified fraction of Fc-modified humanized anti-glypican antibody.

Figure 2:
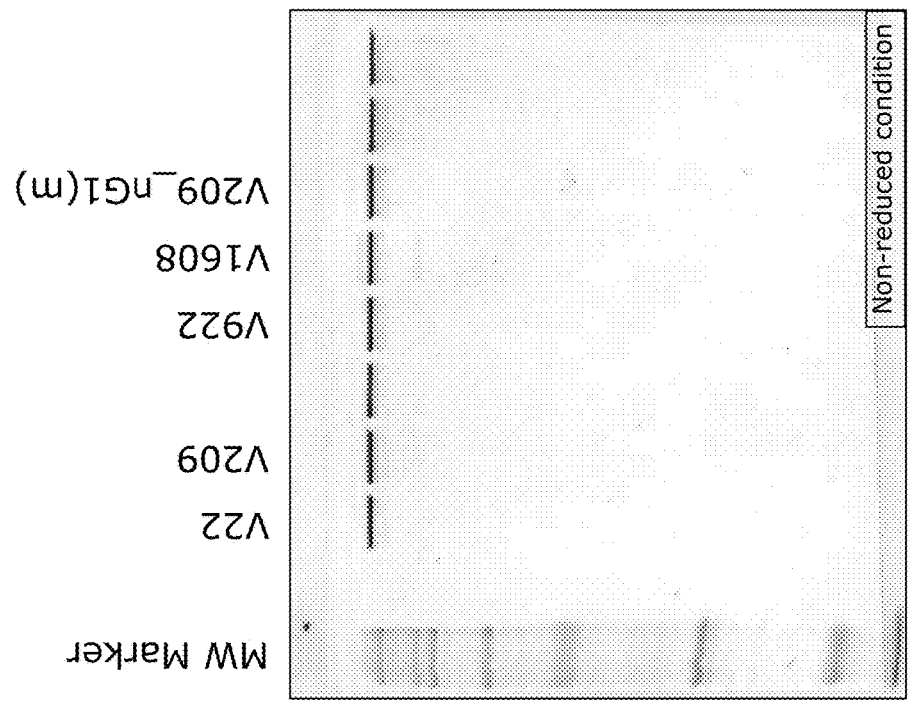
FIG. 2 shows the result of SDS-PAGE analysis of a purified Fc-modified humanized anti-glypican-3 antibody of the invention.
Figure 2:
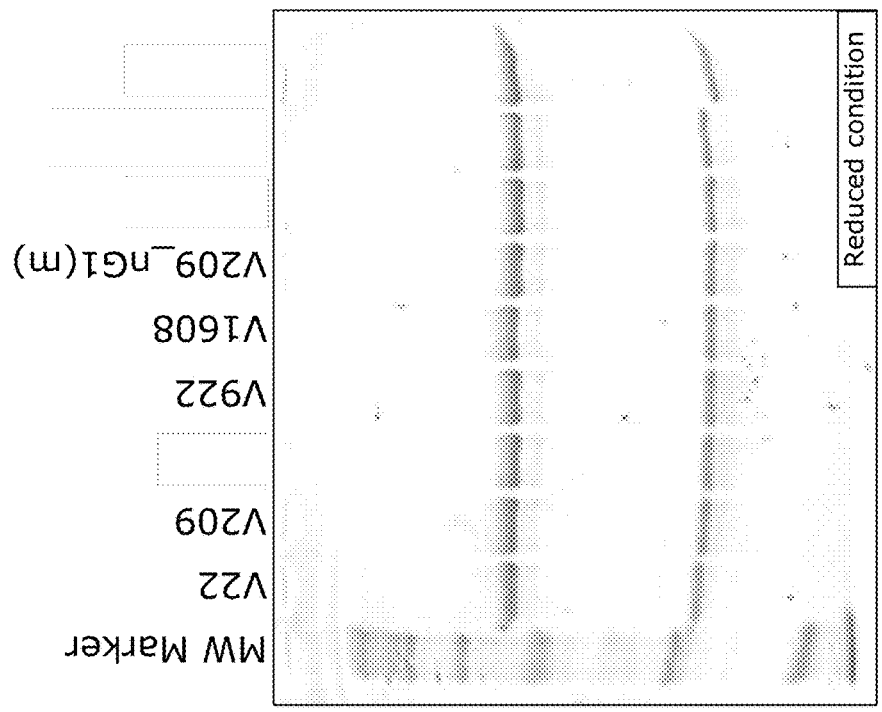

FIG. 2 shows the result of SDS-PAGE (polyacrylamide gel electrophoresis) of a purified Fc-modified humanized anti-glypican antibody of the invention in a known method (Nature, 227, 680, 1970, hereby incorporated by reference in its entirety) to analyze the molecular weight and the degree of purification of the antibody. Each purified Fc-modified humanized anti-glypican antibody provided a single band at a molecular weight of about 150 kDa under a non-reducing condition and provided two bands at about 50 kDa and about 25 kDa under a reducing condition. These molecular weights substantially agree with those presumed from the nucleotide sequence of the H-chain and L-chain cDNAs of the antibody, and further agree with the report that an IgG-type antibody has a molecular weight of about 150 kDa under a non-reducing condition, and an H-chain having a molecular weight of about 50 kDa and an L-chain having a molecular weight of about 25 kDa under a reducing condition, where its intramolecular disulfide bond is cleaved (Antibodies, Chapter 14, Monoclonal Antibodies, hereby incorporated by reference in its entirety). It has been confirmed that each Fc-modified humanized anti-glypican antibody was expressed as an antibody molecule having a correct structure and was purified as such.

Figure 3:
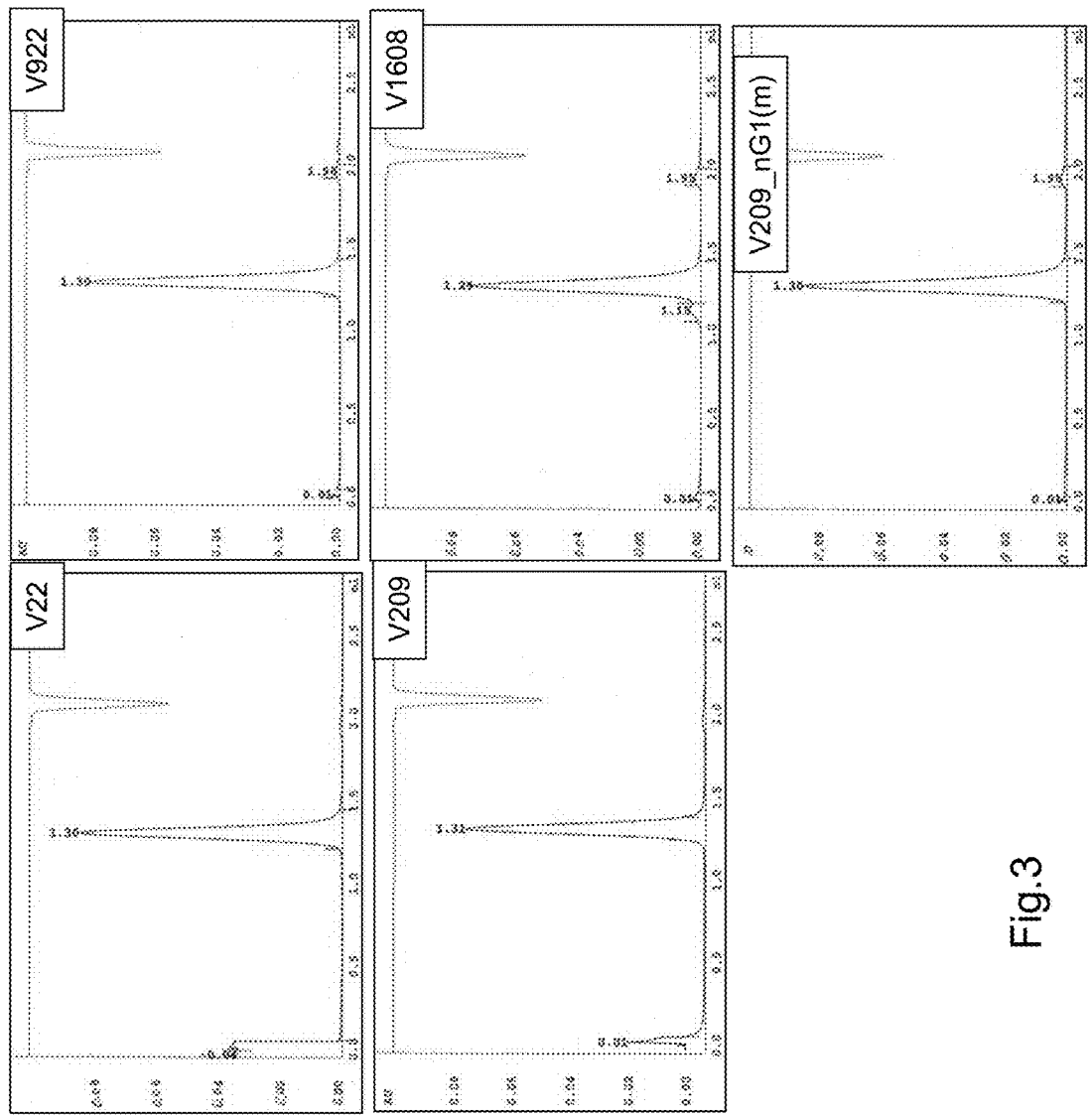
FIG. 3 shows a chromatogram of a purified Fc-modified humanized anti-glypican-3 antibody analyzed through a gel permeation column.

FIG. 3 shows a chromatogram of a purified Fc-modified humanized anti-glypican-3 antibody analyzed through a gel permeation column (Superdex 200 PC3.2/30, by GE Amersham Biosciences).

Example 3: Measurement of ADCC Activity of Fc-Modified Anti-GPC3 Antibody

Example 3-1: cDNA Cloning of Human Glypican-3 (GPC3)

A full-length cDNA coding for human GPC3 was amplified through PCR using Advantage2 kit (CLONETECH)

and, as a template, 1st strand cDNA having been prepared from colon cancer cell line Caco2 in an ordinary manner. Specifically, 50 µl of a reaction solution containing 2 µl of Caco2-derived cDNA, 1 µl of sense primer (GATATC-ATGGCCGGGACCGTGCGCACCGCGT, SEQ ID NO: 17), 1 µl of antisense primer (GCTAGC-TCAGTGCACCA-GGAAGAAGAAGCAC, SEQ ID NO: 18), 5 µl of Advantage2 10×PCR buffer, 8 µl of dNTX mix (1.25 mM) and 1.0 µl of Advantage polymerase Mix, was subjected to 35 cycles of 94° C. 1 min; 63° C. 30 sec; 68° C. 3 min. The PCR amplified product was inserted into a TA vector pGEM-Teasy by the use of pGEM-T Easy Vector System I (Promega). The sequence of the product was confirmed using ABI3100 DNA sequencer. In this way, cDNA coding for the full length of human GPC3 was isolated. The nucleotide sequence of human GPC3 gene is shown in SEQ ID NO:19, and the amino acid sequence of human GPC3 protein is shown in SEQ ID NO:20.

Example 3-2: Preparation of Human Hepatic Cancer Cell Line (SK-03) Expressing Full-Length GPC3

To obtain a cell line for evaluating the biological activity of anti-GPC3 antibody, a human hepatic cell line capable of expressing a full-length GPC3 was established.

One µg of full-length human GPC3 gene expression vector treated with PvuI was mixed with 2 µl of FuGENE (Roche) to form a complex, and then this was added to SK-HEP-1 cells (purchased from ATCC) for gene introduction. The cells were incubated in a $CO_2$ incubator for 24 hours, and then, GPC3-expressing cells were selected using Dulbecco MEM (D-MEM, by SIGMA) containing geneticin (Invitrogen) at a final concentration of 1 mg/ml and 10% FBS. The thus-obtained geneticin-resistant colonies were collected, and the cells were cloned according to a limiting dilution method. The expression of human GPC3 in each cell clone was determined by flow cytometry using chimera GC33 antibody and FITC-labeled goat anti-human IgG antibody (ICN) to obtain a stable expression cell line SK-03 was obtained.

Example 3-3: Measurement of ADCC Activity with Human Peripheral Blood-Derived PBMC

Example 3-3-1: Preparation of Human PBMC Solution

Heparin-added peripheral blood was collected from a healthy person, diluted 2-fold with PBS(−) and overlaid on Ficoll-Paque™ PLUS (Amersham). After centrifugation (500×g, 30 minutes, 20° C.), the interlayer of a monocyte fraction was collected. The monocytes were washed three times and suspended in 10% FBS/RPMI to prepare a human PBMC solution.

Example 3-3-2: Preparation of Target Cells

SK-03 cells were maintained in D-MEM medium (SIGMA) containing 1 mg/ml of geneticin and 10% FBS (ThermoTrace). The cells were peeled from the dish using Cell Dissociation Buffer (Invitrogen), and transferred to each well of a 96-well U-bottomed plate (Falcon) at $1\times10^4$ cells/well, and incubated for 1 day. After the incubation, 5.55 MBq of Chromium-51 was added and the cells were further incubated in a 5% $CO_2$ incubator at 37° C. for 4 hours. The cells were washed once with the medium, and suspended in 50 µl of 10% FBS/RPMI1640 medium to prepare target cells.

Example 3-3-3: Chromium Release Test (ADCC Activity)

Fifty µl of an antibody solution prepared to have a predetermined concentration was added to the target cells, and reacted at room temperature for 15 minutes. Next, 100 µl of the human PBMC solution was added ($5\times10^5$ cells/well), and centrifuged, and then incubated in a 5% $CO_2$ incubator at 37° C. for 4 hours. After the incubation, the plate was centrifuged, and the radioactivity of 100 µl of the culture supernatant was counted with a gamma counter. The specific chromium release ratio of the sample was obtained according to the following formula:

$$\text{Specific Chromium Release Ratio (\%)} = (A-C)\times 100/(B-C)$$

wherein A indicates a mean value of the radioactivity (cpm) in each well; B indicates a mean value of the radioactivity (cpm) of each well, in which 100 µl of aqueous 2% NP-40 solution (Nonidet P-40, Code No. 252-23, by Nacalai Tesque) and 50 µl of 10% FBS/RPMI medium were added to the target cells; C indicates a mean value of the radioactivity (cpm) of each well, in which 150 µl of 10% FBS/RPMI medium was added to the target cells.

The experiment was carried out in triplicate, and the mean value of the ADCC activity (%) of the sample was calculated.

Figure 4:
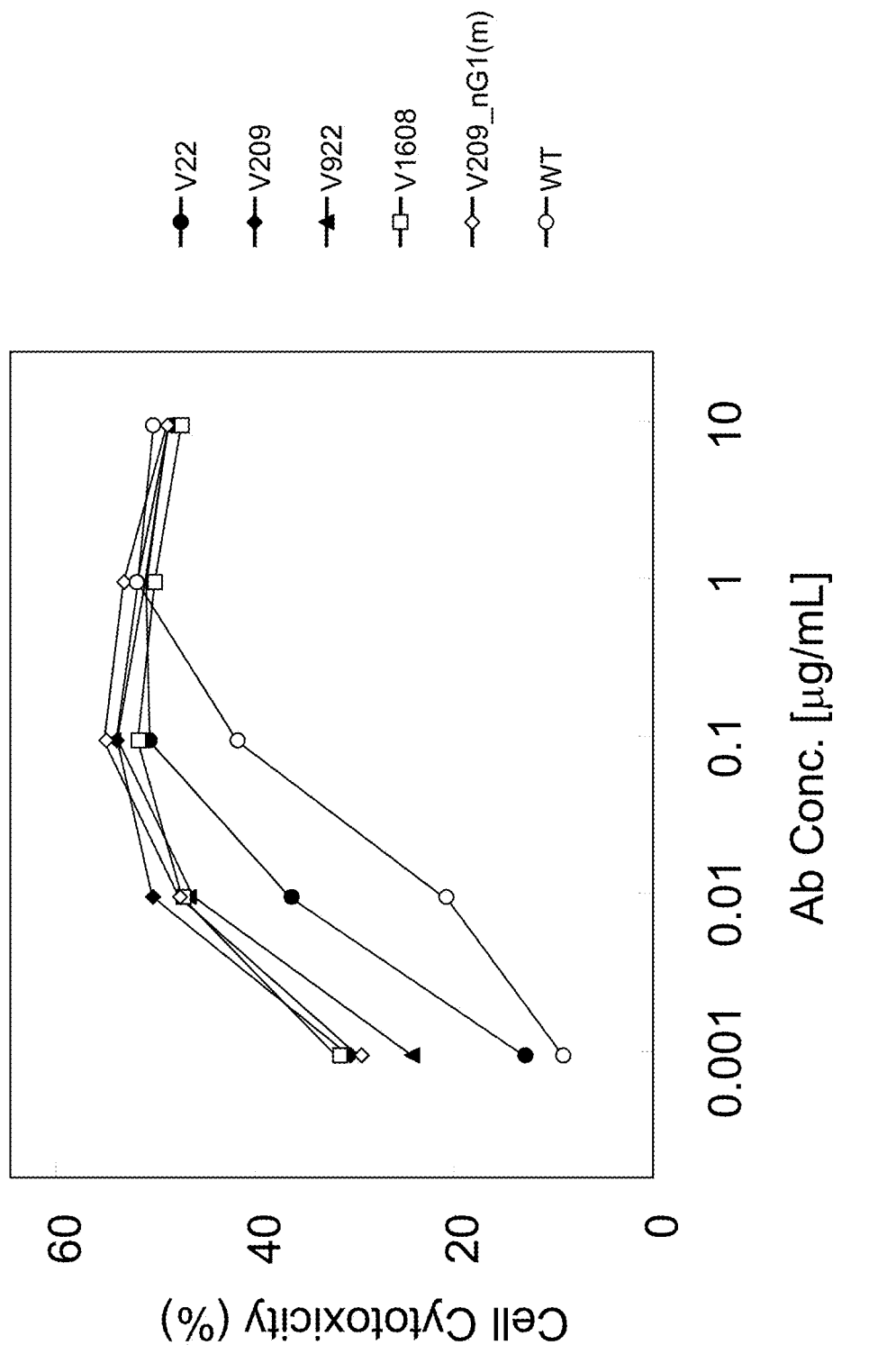
FIG. 4 shows the ADCC activity against SK-03 cells of the Fc-modified and wild-type humanized anti-glypican-3 antibodies, using human peripheral blood-derived PBMC.

The results are shown in FIG. 4. The Fc-modified humanized anti-glypican antibodies V22, V209, V922, V1608 and V209(nGlm(1)) all had enhanced ADCC activity compared to the wild-type antibody (WT). Of those, the activity of V22 was lower than that of the others, but there was found little difference in the activity between V209, V922, V1608 and V209(nGlm(1)).

Example 3-4: Measurement of ADCC Activity Using Mouse Marrow-Derived Effector Cells

Example 3-4-1: Preparation of Mouse Marrow-Derived Effector Cell Suspension Marrow cells were collected from the thigh bone of an SCID mouse (from Nippon Clea, male, 10 weeks old), and suspended in 10% FBS/RPMI1640 medium at a density of $5\times10^5$ cells/ml. Mouse GM-CSF (Pepro Tech) and human IL-2 (Pepro Tech) were added at a final concentration of 10 ng/ml and 50 ng/ml, respectively. The cells were incubated in a 5% $CO_2$ incubator at 37° C. for 5 days. After the incubation, the cells were peeled with a scraper, washed once with the medium, and suspended in 10% FBS/RPMI1640 medium at a density of $5\times10^6$ cells/ml to prepare a mouse marrow-derived effector cell suspension.

Example 3-4-2: Preparation of Target Cells

Human hepatic cancer cells HepG2 (purchased from ATCC) were maintained in RPMI1640 medium (SIGMA) containing 10% FBS (Thermo Trace). The cells were peeled from the dish using Cell Dissociation Buffer (Invitrogen), and transferred to each well of a 96-well U-bottomed plate (Falcon) at a density of $1\times10^4$ cells/well, and incubated for 1 day. After the incubation, 5.55 MBq of Chromium-51 was added and the cells were further incubated in a 5% $CO_2$ incubator at 37° C. for 4 hours. The cells were washed once with the medium, and suspended in 50 µl of 10% FBS/RPMI1640 medium to prepare target cells.

Example 3-4-3: Chromium Release Test (ADCC Activity)

Fifty µl of an antibody solution prepared to have a predetermined concentration was added to the target cells, and reacted at room temperature for 15 minutes. Next, 100 µl of the mouse marrow-derived effector cell suspension was added ($5 \times 10^5$ cells/well), and centrifuged, and then incubated in a 5% $CO_2$ incubator at 37° C. for 4 hours. After the incubation, the plate was centrifuged, and the radioactivity of 100 µl of the culture supernatant was counted with a gamma counter. The specific chromium release ratio of the sample was obtained according to the following formula:

Specific Chromium Release Ratio (%)=$(A-C) \times 100/(B-C)$ wherein A indicates a mean value of the radioactivity (cpm) in each well; B indicates a mean value of the radioactivity (cpm) of each well, in which 100 µl of aqueous 2% NP-40 solution (Nonidet P-40, Code No. 252-23, by Nacalai Tesque) and 50 µl of 10% FBS/RPMI medium were added to the target cells; C indicates a mean value of the radioactivity (cpm) of each well, in which 150 µl of 10% FBS/RPMI medium was added to the target cells.

The experiment was carried out in triplicate, and the mean value of the ADCC activity (%) of the sample was calculated.

Figure 5:
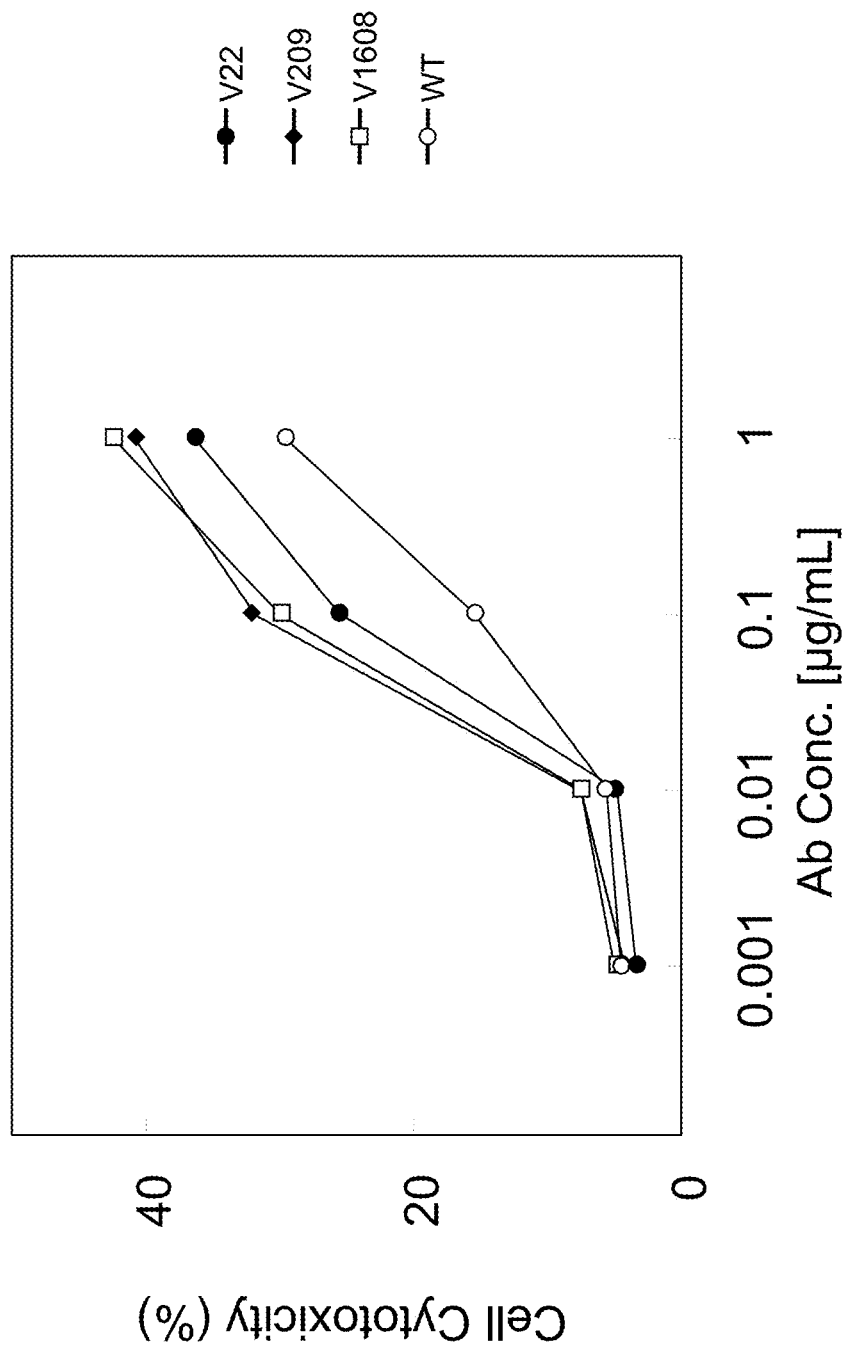
FIG. 5 shows the ADCC activity against HepG2 cells of the Fc-modified and wild-type humanized anti-glypican-3 antibodies, using mouse marrow-derived effector cells.

The results are shown in FIG. 5. The Fc-modified humanized anti-glypican antibodies V22, V209 and V1608 all had enhanced ADCC activity compared to the wild-type antibody (WT).

INDUSTRIAL UTILITY

The Fc-modified humanized anti-glypican-3 antibody is useful in treating cancers, such as hepatic cancer.

What is claimed is:

1. An anti-glypican-3 antibody that comprises a H-chain CDR1 as set forth in SEQ ID NO: 23, a H-chain CDR2 as set forth in SEQ ID NO: 24, and a H-chain CDR3 as set forth in SEQ ID NO: 25; and an L-chain CDR1 as set forth in SEQ ID NO: 26, an L-chain CDR2 as set forth in SEQ ID NO: 27, and an L-chain CDR3 as set forth in SEQ ID NO: 28; and further comprises either (a) or (b):
  (a) an Fc region with aspartic acid at position 239, threonine at position 326, and glutamic acid at position 332 (all positions by EU numbering); or
  (b) an Fc region with aspartic acid at position 239, alanine at position 298, glutamic acid at position 326, and glutamic acid at position 332 (all positions by EU numbering).

2. An anti-glypican-3 antibody that comprises a H-chain CDR1 as set forth in SEQ ID NO: 23, a H-chain CDR2 as set forth in SEQ ID NO: 24, and a H-chain CDR3 as set forth in SEQ ID NO: 25; and an L-chain CDR1 as set forth in SEQ ID NO: 26, an L-chain CDR2 as set forth in SEQ ID NO: 27, and an L-chain CDR3 as set forth in SEQ ID NO: 28; and further comprises either (a) or (b):
  (a) an Fc region in which the amino acid residues at positions 239, 326 and 332 (all positions by EU numbering) are substituted with aspartic acid, threonine, and glutamic acid, respectively; or
  (b) an Fc region in which the amino acid residues at positions 239, 298, 326 and 332 (all positions by EU numbering) are substituted with aspartic acid, alanine, glutamic acid, and glutamic acid, respectively.

3. An anticancer agent comprising the anti-glypican-3 antibody as claimed in claim 1 or 2 and a pharmaceutically acceptable carrier.

4. An anti-glypican-3 antibody that comprises a H-chain CDR1 as set forth in SEQ ID NO: 23, a H-chain CDR2 as set forth in SEQ ID NO: 24, and a H-chain CDR3 as set forth in SEQ ID NO: 25; and an L-chain CDR1 as set forth in SEQ ID NO: 26, an L-chain CDR2 as set forth in SEQ ID NO: 27, and an L-chain CDR3 as set forth in SEQ ID NO: 28; and further comprises (a) or (b):
  (a) a CH2-CH3 domain comprising the amino acid sequence set forth in SEQ ID NO: 37; or
  (b) a CH2-CH3 domain comprising the amino acid sequence set forth in SEQ ID NO: 38.

5. The anti-glypican-3 antibody of claim 1, wherein the antibody comprises (a).

6. An anticancer agent comprising the antibody of claim 5 and a pharmaceutically acceptable carrier.

7. The anti-glypican-3 antibody of claim 1, wherein the antibody comprises (b).

8. An anticancer agent comprising the antibody of claim 7 and a pharmaceutically acceptable carrier.

9. The anti-glypican-3 antibody of claim 4, wherein the antibody comprises (a).

10. The anti-glypican-3 antibody of claim 4, wherein the antibody comprises (b).

* * * * *

SEQUENCE LISTING

```
<160> NUMBER OF SEQ ID NOS: 38

<210> SEQ ID NO 1
<211> LENGTH: 96
<212> TYPE: DNA
<213> ORGANISM: Artificial Sequence
<220> FEATURE:
<223> OTHER INFORMATION: PCR primer

<400> SEQUENCE: 1
agttcaactg gtacgtggac ggcgtggagg tgcataatgc caagacaaag ccgcgggagg      60
agcagtacaa cgccacgtac cgtgtggtca gcgtcc                                96

<210> SEQ ID NO 2
<211> LENGTH: 93
<212> TYPE: DNA
<213> ORGANISM: Artificial Sequence
<220> FEATURE:
<223> OTHER INFORMATION: PCR primer

<400> SEQUENCE: 2
tctcccggac ccctgaggtc acatgcgtgg tggtggacgt gagccacgaa gaccctgagg      60
tcaagttcaa ctggtacgtg gacggcgtgg agg                                   93

<210> SEQ ID NO 3
<211> LENGTH: 97
<212> TYPE: DNA
<213> ORGANISM: Artificial Sequence
<220> FEATURE:
<223> OTHER INFORMATION: PCR primer

<400> SEQUENCE: 3
gcacctgagc tcctgggggg accggacgtc ttcctcttcc ccccaaaacc caaggacacc      60
ctcatgatct cccggacccc tgaggtcaca tgcgtgg                               97

<210> SEQ ID NO 4
<211> LENGTH: 94
<212> TYPE: DNA
<213> ORGANISM: Artificial Sequence
<220> FEATURE:
<223> OTHER INFORMATION: PCR primer

<400> SEQUENCE: 4
```

```
ggagaccttg cacttgtact ccttgccatt cagccagtcc tggtgcagga cggtgaggac    60
gctgaccaca cggtacgtgg cgttgtactg ctcc                                94

<210> SEQ ID NO 5
<211> LENGTH: 91
<212> TYPE: DNA
<213> ORGANISM: Artificial Sequence
<220> FEATURE:
<223> OTHER INFORMATION: PCR primer

<400> SEQUENCE: 5
ggctgccctt tggctttgga gatggttttc tcctcgggca gtgggagggc tttgttggag    60
accttgcact tgtactcctt gccattcagc c                                   91

<210> SEQ ID NO 6
<211> LENGTH: 91
<212> TYPE: DNA
<213> ORGANISM: Artificial Sequence
<220> FEATURE:
<223> OTHER INFORMATION: PCR primer

<400> SEQUENCE: 6
ggctgccctt tggctttgga gatggttttc tcctcggggg ctgggagggc tttgttggag    60
accttgcact tgtactcctt gccattcagc c                                   91

<210> SEQ ID NO 7
<211> LENGTH: 91
<212> TYPE: DNA
<213> ORGANISM: Artificial Sequence
<220> FEATURE:
<223> OTHER INFORMATION: PCR primer

<400> SEQUENCE: 7
ggctgccctt tggctttgga gatggttttc tcctcggggg ctgggagggc ggtgttggag    60
accttgcact tgtactcctt gccattcagc c                                   91

<210> SEQ ID NO 8
<211> LENGTH: 91
<212> TYPE: DNA
<213> ORGANISM: Artificial Sequence
<220> FEATURE:
<223> OTHER INFORMATION: PCR primer

<400> SEQUENCE: 8
ggctgccctt tggctttgga gatggttttc tcctcggggg ctgggagggc ctcgttggag    60
accttgcact tgtactcctt gccattcagc c                                   91

<210> SEQ ID NO 9
<211> LENGTH: 81
<212> TYPE: DNA
<213> ORGANISM: Artificial Sequence
<220> FEATURE:
<223> OTHER INFORMATION: PCR primer

<400> SEQUENCE: 9
gagctccccg ggatggggge agggtgtaca cctgtggttc tcggggctgc cctttggctt    60
tggagatggt tttctcctcg g                                              81

<210> SEQ ID NO 10
<211> LENGTH: 1422
<212> TYPE: DNA
```

<213> ORGANISM: Artificial Sequence
<220> FEATURE:
<223> OTHER INFORMATION: humanized antibody H-chain

<400> SEQUENCE: 10

```
gaattccacc atggactgga cctggaggtt cctctttgtg gtggcagcag ctacaggtgt      60
ccagtcccag gtgcagctgg tgcagtctgg agctgaggtg aagaagcctg ggcctcagt     120
gaaggtctcc tgcaaggctt ctggatacac cttcaccgac tatgaaatgc actgggtgcg    180
acaggcccct ggacaagggc ttgagtggat gggagctctt gatcctaaaa ctggtgatac    240
tgcctacagt cagaagttca agggcagagt cacgctgacc gcggacaaat ccacgagcac    300
agcctacatg gagctgagca gcctgacatc tgaggacacg gccgtgtatt actgtacaag    360
attctactcc tatacttact ggggccaggg aaccctggtc accgtctcct cagctagcac    420
caagggccca tcggtcttcc ccctggcacc ctcctccaag agcacctctg ggggcacagc    480
ggccctgggc tgcctggtca aggactactt ccccgaaccg gtgacggtgt cgtggaactc    540
aggcgccctg accagcggcg tgcacacctt cccggctgtc ctacagtcct caggactcta    600
ctccctcagc agcgtggtga ccgtgccctc cagcagcttg ggcacccaga cctacatctg    660
caacgtgaat cacaagccca gcaacaccaa ggtggacaag aaagttgagc ccaaatcttg    720
tgacaaaact cacacatgcc caccgtgccc agcacctgaa ctcctggggg gaccgtcagt    780
cttcctcttc cccccaaaac ccaaggacac cctcatgatc tcccggaccc ctgaggtcac    840
atgcgtggtg gtggacgtga gccacgaaga ccctgaggtc aagttcaact ggtacgtgga    900
cggcgtggag gtgcataatg ccaagacaaa gccgcgggag gagcagtaca acagcacgta    960
ccgtgtggtc agcgtcctca ccgtcctgca ccaggactgg ctgaatggca aggagtacaa   1020
gtgcaaggtc tccaacaaag ccctcccagc ccccatcgag aaaaccatct ccaaagccaa   1080
agggcagccc cgagaaccac aggtgtacac cctgccccca tcccgggatg agctgaccaa   1140
gaaccaggtc agcctgacct gcctggtcaa aggcttctat cccagcgaca tcgccgtgga   1200
gtgggagagc aatgggcagc cggagaacaa ctacaagacc acgcctcccg tgctggactc   1260
cgacggctcc ttcttcctct acagcaagct caccgtggac aagagcaggt ggcagcaggg   1320
gaacgtcttc tcatgctccg tgatgcatga ggctctgcac aaccactaca cgcagaagag   1380
cctctccctg tctccgggta aatgataagc ggccgcggat cc                      1422
```

<210> SEQ ID NO 11
<211> LENGTH: 45
<212> TYPE: DNA
<213> ORGANISM: Artificial Sequence
<220> FEATURE:
<223> OTHER INFORMATION: PCR primer

<400> SEQUENCE: 11

```
gctagcacca agggcccatc ggtcttcccc ctggcaccct cctcc                     45
```

<210> SEQ ID NO 12
<211> LENGTH: 44
<212> TYPE: DNA
<213> ORGANISM: Artificial Sequence
<220> FEATURE:
<223> OTHER INFORMATION: PCR primer

<400> SEQUENCE: 12

```
gagctcaggt gctgggcacg gtgggcatgt gtgagttttg tcac                      44
```

<210> SEQ ID NO 13
<211> LENGTH: 3067
<212> TYPE: DNA
<213> ORGANISM: Artificial Sequence
<220> FEATURE:
<223> OTHER INFORMATION: Humanized antibody L-chain

<400> SEQUENCE: 13

| | | | | | |
|---|---|---|---|---|---|
| aagcttgcat | gcctgcaggt | cgactctaga | ggatccgtcg | acattgatta | ttgactagtt | 60 |
| attaatagta | atcaattacg | gggtcattag | ttcatagccc | atatatggag | ttccgcgtta | 120 |
| cataacttac | ggtaaatggc | ccgcctggct | gaccgcccaa | cgacccccgc | ccattgacgt | 180 |
| caataatgac | gtatgttccc | atagtaacgc | caatagggac | tttccattga | cgtcaatggg | 240 |
| tggagtattt | acggtaaact | gcccacttgg | cagtacatca | agtgtatcat | atgccaagta | 300 |
| cgccccctat | tgacgtcaat | gacggtaaat | ggcccgcctg | gcattatgcc | cagtacatga | 360 |
| ccttatggga | ctttcctact | tggcagtaca | tctacgtatt | agtcatcgct | attaccatgg | 420 |
| tcgaggtgag | ccccacgttc | tgcttcactc | tccccatctc | ccccccctcc | ccacccccaa | 480 |
| ttttgtattt | atttattttt | taattatttt | gtgcagcgat | gggggcgggg | gggggggggg | 540 |
| ggcgcgcgcc | aggcggggcg | gggcggggcg | aggggcgggg | cggggcgagg | cggagaggtg | 600 |
| cggcggcagc | caatcagagc | ggcgcgctcc | gaaagtttcc | ttttatggcg | aggcggcggc | 660 |
| ggcggcggcc | ctataaaaag | cgaagcgcgc | ggcgggcggg | agtcgctgcg | cgctgccttc | 720 |
| gccccgtgcc | ccgctccgcc | gccgcctcgc | gccgcccgcc | ccggctctga | ctgaccgcgt | 780 |
| tactcccaca | ggtgagcggg | cgggacggcc | cttctcctcc | gggctgtaat | tagcgcttgg | 840 |
| tttaatgacg | gcttgtttct | tttctgtggc | tgcgtgaaag | ccttgagggg | ctccgggagg | 900 |
| gccctttgtg | cgggggggagc | ggctcggggg | gtgcgtgcgt | gtgtgtgtgc | gtggggagcg | 960 |
| ccgcgtgcgg | ctccgcgctg | cccggcggct | gtgagcgctg | cgggcgcggc | gcgggctttg | 1020 |
| tgcgctccg | cagtgtgcgc | gaggggagcg | cggccggggg | cggtgccccg | cggtgcgggg | 1080 |
| ggggctgcga | ggggaacaaa | ggctgcgtgc | ggggtgtgtg | cgtggggggg | tgagcagggg | 1140 |
| gtgtgggcgc | gtcggtcggg | ctgcaacccc | ccctgcaccc | ccctccccga | gttgctgagc | 1200 |
| acggcccggc | ttcgggtgcg | gggctccgta | cggggcgtgg | cgcggggctc | gccgtgccgg | 1260 |
| gcgggggtg | gcggcaggtg | ggggtgccgg | gcggggcggg | gccgcctcgg | gccggggagg | 1320 |
| gctcggggga | ggggcgcggc | ggcccccgga | gcgccgcgcg | ctgtcgaggc | gcggcgagcc | 1380 |
| gcagccattg | cctttttatgg | taatcgtgcg | agagggcgca | gggacttcct | ttgtcccaaa | 1440 |
| tctgtgcgga | gccgaaatct | gggaggcgcc | gccgcacccc | ctctagcggg | cgcggggcga | 1500 |
| agcggtgcgg | cgccggcagg | aaggaaatgg | gcgggagggg | ccttcgtgcg | tcgccgcgcc | 1560 |
| gccgtccccct | tctccctctc | cagcctcggg | gctgtccgcg | ggggacggc | tgccttcggg | 1620 |
| ggggacgggg | cagggcgggg | ttcggcttct | ggcgtgtgac | cggcggctct | agagcctctg | 1680 |
| ctaaccatgt | tcatgccttc | ttctttttcc | tacagctcct | gggcaacgtg | ctggttattg | 1740 |
| tgctgtctca | tcatttggc | aaagaattcc | tcgagccacc | atgaggctcc | ctgctcagct | 1800 |
| cctggggctg | ctaatgctct | gggtctctgg | atccagtggg | gatgttgtga | tgactcagtc | 1860 |
| tccactctcc | ctgcccgtca | cccctggaga | gccggcctcc | atctcctgca | gatctagtca | 1920 |
| gagccttgta | cacagtaata | ggaacaccta | tttacattgg | tacctgcaga | agccagggca | 1980 |
| gtctccacag | ctcctgatct | ataaagtttc | caaccgattt | tctggggtcc | ctgacaggtt | 2040 |
| cagtggcagt | ggatcaggca | cagatttac | actgaaaatc | agcagagtgg | aggctgagga | 2100 |

```
tgttggggtt tattactgct ctcaaaatac acatgttcct cctacgtttg gccaggggac      2160
caagctggag atcaaacgta cggtggctgc accatctgtc ttcatcttcc cgccatctga      2220
tgagcagttg aaatctggaa ctgcctctgt tgtgtgcctg ctgaataact tctatcccag      2280
agaggccaaa gtacagtgga aggtggataa cgccctccaa tcgggtaact cccaggagaa      2340
tgtcacagag caggacagca aggacagcac ctacagcctc agcagcaccc tgacgctgag      2400
caaagcagac tacgagaaac acaaagtcta cgcctgcgaa gtcacccatc agggcctgag      2460
ctcgcccgtc acaaagagct tcaacagggg agagtgttga taagtcgagg tcgaggaatt      2520
cactcctcag gtgcaggctg cctatcagaa ggtggtggct ggtgtggcca atgccctggc      2580
tcacaaatac cactgagatc ttttttccctc tgccaaaaat tatggggaca tcatgaagcc      2640
ccttgagcat ctgacttctg gctaataaag gaaatttatt ttcattgcaa tagtgtgttg      2700
gaattttttg tgtctctcac tcggaaggac atatgggagg gcaaatcatt taaaacatca      2760
gaatgagtat ttggtttaga gtttggcaac atatgcccat atgctggctg ccatgaacaa      2820
aggttggcta taaagaggtc atcagtatat gaaacagccc cctgctgtcc attccttatt      2880
ccatagaaaa gccttgactt gaggttagat ttttttttata ttttgttttg tgttattttt      2940
ttctttaaca tccctaaaat tttccttaca tgttttacta gccagatttt tcctcctctc      3000
ctgactactc ccagtcatag ctgtccctct tctcttatgg agatccctcg acctgcagcc      3060
caagctt                                                                3067

<210> SEQ ID NO 14
<211> LENGTH: 39
<212> TYPE: DNA
<213> ORGANISM: Artificial Sequence
<220> FEATURE:
<223> OTHER INFORMATION: PCR primer

<400> SEQUENCE: 14
gggaggagat gaccaagaac caggtcaccc tgacctgcc                              39

<210> SEQ ID NO 15
<211> LENGTH: 42
<212> TYPE: DNA
<213> ORGANISM: Artificial Sequence
<220> FEATURE:
<223> OTHER INFORMATION: PCR primer

<400> SEQUENCE: 15
tttgcggccg cttatcattt acccggagac agggagaggc tc                          42

<210> SEQ ID NO 16
<211> LENGTH: 40
<212> TYPE: PRT
<213> ORGANISM: Homo sapiens

<400> SEQUENCE: 16

Ala Glu Leu Ala Tyr Asp Leu Asp Val Asp Asp Ala Pro Gly Asn Ser
 1               5                  10                  15

Gln Gln Ala Thr Pro Lys Asp Asn Glu Ile Ser Thr Phe His Asn Leu
            20                  25                  30

Gly Asn Val His Ser Pro Leu Lys
        35                  40

<210> SEQ ID NO 17
<211> LENGTH: 31
<212> TYPE: DNA
```

```
<213> ORGANISM: Artificial Sequence
<220> FEATURE:
<223> OTHER INFORMATION: PCR primer

<400> SEQUENCE: 17
gatatcatgg ccgggaccgt gcgcaccgcg t                              31

<210> SEQ ID NO 18
<211> LENGTH: 31
<212> TYPE: DNA
<213> ORGANISM: Artificial Sequence
<220> FEATURE:
<223> OTHER INFORMATION: PCR primer

<400> SEQUENCE: 18
gctagctcag tgcaccagga agaagaagca c                              31

<210> SEQ ID NO 19
<211> LENGTH: 1743
<212> TYPE: DNA
<213> ORGANISM: Homo sapiens

<400> SEQUENCE: 19
atggccggga ccgtgcgcac cgcgtgcttg gtggtggcga tgctgctcag cttggacttc    60
ccgggacagg cgcagccccc gccgccgccg ccggacgcca cctgtcacca agtccgctcc   120
ttcttccaga gactgcagcc cggactcaag tgggtgccag aaactcccgt gccaggatca   180
gatttgcaag tatgtctccc taagggccca acatgctgct caagaaagat ggaagaaaaa   240
taccaactaa cagcacgatt gaacatggaa cagctgcttc agtctgcaag tatggagctc   300
aagttcttaa ttattcagaa tgctgcggtt ttccaagagg cctttgaaat tgttgttcgc   360
catgccaaga actacaccaa tgccatgttc aagaacaact acccaagcct gactccacaa   420
gcttttgagt ttgtgggtga attttttcaca gatgtgtctc tctacatctt gggttctgac   480
atcaatgtag atgacatggt caatgaattg tttgacagcc tgtttccagt catctatacc   540
cagctaatga acccaggcct gcctgattca gccttggaca tcaatgagtg cctccgagga   600
gcaagacgtg acctgaaagt atttgggaat tcccccaagc ttattatgac ccaggttttcc   660 aagtcactgc aagtcactag gatcttcctt caggctctga atcttggaat tgaagtgatc   720
aacacaactg atcacctgaa gttcagtaag gactgtggcc aatgctcac cagaatgtgg   780 tactgctctt actgccaggg actgatgatg gttaaaccct gtggcggtta ctgcaatgtg   840
gtcatgcaag gctgtatggc aggtgtggtg gagattgaca gtactggag agaatacatt   900 ctgtcccttg aagaacttgt gaatggcatg tacagaatct atgacatgga gaacgtactg   960
cttggtctct tttcaacaat ccatgattct atccagtatg tccagaagaa tgcaggaaag  1020
ctgaccacca ctattggcaa gttatgtgcc cattctcaac aacgccaata tagatctgct  1080
tattatcctg aagatctctt tattgacaag aaagtattaa agttgctca tgtagaacat  1140 gaagaaacct atccagccg aagaagggaa ctaattcaga agttgaagtc tttcatcagc  1200
ttctatagtg cttttgcctgg ctacatctgc agccatagcc ctgtggcgga aaacgacacc  1260 cttttgctgga tggacaaga actcgtggag agatacagcc aaaaggcagc aaggaatgga  1320
atgaaaaacc agttcaatct ccatgagctg aaaatgaagg gccctgagcc agtggtcagt  1380
caaattattg acaaactgaa gcacattaac cagctcctga gaaccatgtc tatgcccaaa  1440
ggtagagttc tggataaaaa cctggatgag gaagggtttg aaagtggaga ctgcggtgat  1500
gatgaagatg agtgcattgg aggctctggt gatggaatga taaaagtgaa gaatcagctc  1560
```

```
cgcttccttg cagaactggc ctatgatctg gatgtggatg atgcgcctgg aaacagtcag    1620
caggcaactc cgaaggacaa cgagataagc acctttcaca acctcgggaa cgttcattcc    1680
ccgctgaagc ttctcaccag catggccatc tcggtggtgt gcttcttctt cctggtgcac    1740
tga                                                                  1743

<210> SEQ ID NO 20
<211> LENGTH: 580
<212> TYPE: PRT
<213> ORGANISM: Homo sapiens

<400> SEQUENCE: 20

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335
```

```
Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 21
<211> LENGTH: 115
<212> TYPE: PRT
<213> ORGANISM: Artificial Sequence
<220> FEATURE:
<223> OTHER INFORMATION: Humanized antibody H-chain variable region

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110
```

Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Humanized antibody L-chain variable region

<400> SEQUENCE: 22

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 23
<211> LENGTH: 5
<212> TYPE: PRT
<213> ORGANISM: Mus musculus

<400> SEQUENCE: 23

Asp Tyr Glu Met His
1               5

<210> SEQ ID NO 24
<211> LENGTH: 17
<212> TYPE: PRT
<213> ORGANISM: Mus musculus

<400> SEQUENCE: 24

Ala Leu Asp Pro Lys Thr Gly Asp Thr Ala Tyr Ser Gln Lys Phe Lys
1               5                   10                  15

Gly

<210> SEQ ID NO 25
<211> LENGTH: 6
<212> TYPE: PRT
<213> ORGANISM: Mus musculus

<400> SEQUENCE: 25

Phe Tyr Ser Tyr Thr Tyr
1               5

<210> SEQ ID NO 26
<211> LENGTH: 16
<212> TYPE: PRT
<213> ORGANISM: Mus musculus

<400> SEQUENCE: 26

Arg Ser Ser Gln Ser Leu Val His Ser Asn Gly Asn Thr Tyr Leu His

```
<210> SEQ ID NO 27
<211> LENGTH: 7
<212> TYPE: PRT
<213> ORGANISM: Mus musculus

<400> SEQUENCE: 27

Lys Val Ser Asn Arg Phe Ser
1               5

<210> SEQ ID NO 28
<211> LENGTH: 9
<212> TYPE: PRT
<213> ORGANISM: Mus musculus

<400> SEQUENCE: 28

Ser Gln Asn Thr His Val Pro Pro Thr
1               5

<210> SEQ ID NO 29
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
              245                 250                 255

Val Thr Cys Val Val Val Asp Val Ser His Glu Asp Pro Glu Val Lys
          260                 265                 270

Phe Asn Trp Tyr Val Asp Gly Val Glu Val His Asn Ala Lys Thr Lys
      275                 280                 285

Pro Arg Glu Glu Gln Tyr Asn Ser Thr Tyr Arg Val Val Ser Val Leu
  290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
              325                 330                 335

Ala Lys Gly Gln Pro Arg Glu Pro Gln Val Tyr Thr Leu Pro Pro Ser
          340                 345                 350

Arg Asp Glu Leu Thr Lys Asn Gln Val Ser Leu Thr Cys Leu Val Lys
      355                 360                 365

Gly Phe Tyr Pro Ser Asp Ile Ala Val Glu Trp Glu Ser Asn Gly Gln
  370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
              405                 410                 415

Gln Gly Asn Val Phe Ser Cys Ser Val Met His Glu Ala Leu His Asn
          420                 425                 430

His Tyr Thr Gln Lys Ser Leu Ser Leu Ser Pro Gly Lys
      435                 440                 445

<210> SEQ ID NO 30
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 30

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asp Tyr
              20                  25                  30

Glu Met His Trp Val Arg Gln Ala Pro Gly Gln Gly Leu Glu Trp Met
          35                  40                  45

Gly Ala Leu Asp Pro Lys Thr Gly Asp Thr Ala Tyr Ser Gln Lys Phe
      50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
              85                  90                  95

Thr Arg Phe Tyr Ser Tyr Thr Tyr Trp Gly Gln Gly Thr Leu Val Thr
          100                 105                 110

Val Ser Ser Ala Ser Thr Lys Gly Pro Ser Val Phe Pro Leu Ala Pro
      115                 120                 125

Ser Ser Lys Ser Thr Ser Gly Gly Thr Ala Ala Leu Gly Cys Leu Val
  130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Leu Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 31
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80
```

```
Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 32
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 32
```

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
             20                  25                  30

Glu Met His Trp Val Arg Gln Ala Pro Gly Gln Gly Leu Glu Trp Met
         35                  40                  45

Gly Ala Leu Asp Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
             85                  90                  95

Thr Arg Phe Tyr Ser Tyr Thr Tyr Trp Gly Gln Gly Thr Leu Val Thr
             100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
         130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Thr Ala Leu Pro Ala Pro Glu Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Asp Glu Leu Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
```

His Tyr Thr Gln Lys Ser Leu Ser Leu Ser Pro Gly Lys
            435                 440                 445

<210> SEQ ID NO 33
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Glu Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser

```
                340                 345                 350
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 34
<211> LENGTH: 217
<212> TYPE: PRT
<213> ORGANISM: Homo sapiens

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 35
<211> LENGTH: 217
<212> TYPE: PRT
<213> ORGANISM: Homo sapiens

<400> SEQUENCE: 35

Ala Pro Glu Leu Leu Gly Gly Pro Asp Val Phe Leu Phe Pro Pro Lys
```

```
1               5                   10                  15
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Leu Pro Glu Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
        210                 215

<210> SEQ ID NO 36
<211> LENGTH: 217
<212> TYPE: PRT
      <213> ORGANISM: Homo sapiens

<400> SEQUENCE: 36

Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ala Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Glu Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160
```

```
Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
210                 215
```

<210> SEQ ID NO 37
<211> LENGTH: 217
<212> TYPE: PRT
<213> ORGANISM: Homo sapiens

<400> SEQUENCE: 37

```
Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Thr
                85                  90                  95

Ala Leu Pro Ala Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 38
<211> LENGTH: 217
<212> TYPE: PRT
<213> ORGANISM: Homo sapiens

<400> SEQUENCE: 38

```
Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

-continued

```
Val Asp Gly Val Glu Val His Asn Ala Lys Thr Lys Pro Arg Glu Glu
    50              55                  60
Gln Tyr Asn Ala Thr Tyr Arg Val Val Ser Val Leu Thr Val Leu His
65              70                  75                  80
Gln Asp Trp Leu Asn Gly Lys Glu Tyr Lys Cys Lys Val Ser Asn Glu
            85                  90                  95
Ala Leu Pro Ala Pro Glu Glu Lys Thr Ile Ser Lys Ala Lys Gly Gln
            100                 105             110
Pro Arg Glu Pro Gln Val Tyr Thr Leu Pro Pro Ser Arg Asp Glu Leu
        115                 120             125
Thr Lys Asn Gln Val Ser Leu Thr Cys Leu Val Lys Gly Phe Tyr Pro
    130                 135             140
Ser Asp Ile Ala Val Glu Trp Glu Ser Asn Gly Gln Pro Glu Asn Asn
145             150                 155                 160
Tyr Lys Thr Thr Pro Pro Val Leu Asp Ser Asp Gly Ser Phe Phe Leu
                165             170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215
```